(12) United States Patent
Bøggild-Damkvist et al.

(10) Patent No.: US 11,458,259 B2
(45) Date of Patent: Oct. 4, 2022

(54) INJECTION LOCATION AND/OR DOSAGE DETERMINATION DEVICE AND SYSTEM FOR A LIQUID DRUG ADMINISTRATION DEVICE OR SYSTEM

(71) Applicant: Nordic Healthcare Advisory ApS, Ølstykke (DK)

(72) Inventors: David Tobias Bøggild-Damkvist, Ølstykke (DK); Rasmus Thomas Tjalk-Bøggild, Frederiksberg (DK)

(73) Assignee: Nordic Healthcare Advisory ApS, Ølstykke (DK)

( * ) Notice: Subject to any disclaimer, the term of this patent is extended or adjusted under 35 U.S.C. 154(b) by 365 days.

(21) Appl. No.: 16/500,983

(22) PCT Filed: Apr. 6, 2018

(86) PCT No.: PCT/IB2018/052412
§ 371 (c)(1),
(2) Date: Oct. 4, 2019

(87) PCT Pub. No.: WO2018/185727
PCT Pub. Date: Oct. 11, 2018

(65) Prior Publication Data
US 2020/0030551 A1    Jan. 30, 2020

Related U.S. Application Data

(63) Continuation of application No. 15/481,087, filed on Apr. 6, 2017, now abandoned.

(51) Int. Cl.
*A61M 5/42*    (2006.01)
*A61M 5/20*    (2006.01)
(Continued)

(52) U.S. Cl.
CPC .............. *A61M 5/427* (2013.01); *A61M 5/20* (2013.01); *A61M 5/31525* (2013.01);
(Continued)

(58) Field of Classification Search
CPC ...... A61M 5/31525; A61M 2205/3327; A61M 5/31568; A61M 2205/3317;
(Continued)

(56) References Cited

U.S. PATENT DOCUMENTS

| 6,156,008 A | 12/2000 | Castellano |
| 2007/0012322 A1 | 1/2007 | Ragg |

(Continued)

FOREIGN PATENT DOCUMENTS

| AU | B-53957/79 | 10/1983 |
| DE | 102004037207 A1 | 4/2005 |

(Continued)

OTHER PUBLICATIONS

Blanco M., et al., "Prevalence and Risk Factors in Lipohypertrophy in Insulin-Injecting Patients With Diabetes," Diabetes & Metabolism, Oct. 2013, vol. 39, Issue 5, pp. 445-453; downloaded at http://www.ciabet-metabolism.com/article/S1262-363(13)00121-3/fulltext.com (abstract only) (2 pages).

(Continued)

*Primary Examiner* — Deanna K Hall
(74) *Attorney, Agent, or Firm* — Nixon Peabody LLP

(57) ABSTRACT

A position determination device and system for determining and registering an injection location of a liquid drug administered on a body part of a user. The position determination device and system includes a position determination element configured to provide a position signal representing a current location of the position determination device, and one or more processing units configured to derive data representing an actual injection location based on the user in response to (Continued)

a current location being determined by the position determination unit. The position determination device can be further configured for determining a dosage activity performed by a liquid drug administration device based on obtaining at least one vibration signal from a vibration determination element.

9 Claims, 19 Drawing Sheets

(51) Int. Cl.
 A61M 5/32 (2006.01)
 A61M 5/315 (2006.01)
(52) U.S. Cl.
 CPC ...... *A61M 5/31568* (2013.01); *A61M 5/3202* (2013.01); *A61M 2205/13* (2013.01); *A61M 2205/3306* (2013.01); *A61M 2205/3317* (2013.01); *A61M 2205/3327* (2013.01); *A61M 2205/3375* (2013.01); *A61M 2205/35* (2013.01); *A61M 2205/3584* (2013.01); *A61M 2205/43* (2013.01); *A61M 2205/50* (2013.01); *A61M 2205/502* (2013.01); *A61M 2205/52* (2013.01); *A61M 2205/581* (2013.01); *A61M 2205/583* (2013.01); *A61M 2205/584* (2013.01); *A61M 2205/59* (2013.01); *A61M 2205/70* (2013.01)
(58) Field of Classification Search
 CPC ...... A61M 2205/3375; A61M 2205/43; A61M 2205/581
 See application file for complete search history.

(56) References Cited

U.S. PATENT DOCUMENTS

| | | |
|---|---|---|
| 2011/0288527 A1 | 11/2011 | Pesach |
| 2014/0207099 A1 | 7/2014 | Nagar |
| 2014/0379358 A1 | 12/2014 | Chovanda |
| 2015/0051538 A1 | 2/2015 | Hata |
| 2015/0085286 A1 | 3/2015 | Whalley |
| 2015/0290396 A1 | 10/2015 | Nagar |
| 2016/0012205 A1 | 1/2016 | Saint |
| 2016/0113568 A1 | 4/2016 | Macchi |
| 2016/0213853 A1 | 7/2016 | Despa |
| 2017/0136185 A1 | 5/2017 | Rios |
| 2018/0311445 A1 | 11/2018 | Boggild-Damkvist |

FOREIGN PATENT DOCUMENTS

| | | |
|---|---|---|
| DK | 178729 B1 | 12/2016 |
| EP | 2753387 A1 | 7/2014 |
| EP | 2926846 A1 | 10/2015 |
| EP | 3188061 A2 | 7/2017 |
| FR | 2980977 A1 | 4/2013 |
| WO | WO 2009/089028 A2 | 7/2009 |
| WO | WO 2013/034716 A1 | 3/2013 |
| WO | WO 2013/069305 A1 | 5/2013 |
| WO | WO 2014/023763 A1 | 2/2014 |
| WO | WO 2014/145535 A2 | 9/2014 |
| WO | WO 2014/161952 A1 | 10/2014 |
| WO | WO 2015/136564 A1 | 3/2015 |
| WO | WO 2015/085019 A1 | 6/2015 |
| WO | WO 2015/136564 A1 | 9/2015 |
| WO | WO 2016/071912 A1 | 5/2016 |
| WO | WO 2016/118736 A1 | 7/2016 |
| WO | WO 2016/140853 A1 | 9/2016 |
| WO | WO 2017/013463 A1 | 1/2017 |

OTHER PUBLICATIONS

Anders H. Frid, MD et al.; New Insulin Delivery Recommendations; Downloaded at http://www.mayoclinicproceedings.org/article/S0025-6196(16)30321-4/abstract); Dated Sep. 2016; (25 pages).
National Institutes of Health Clinical Center; NIH Clinical Center Patient Education Materials Giving a Subcutaneous Injection; Downloaded at http://www.cc.nih.gov/ccc/patient_education/pepubs/subq.pdf; Dated Jul. 2016 (3 pages).
International Search Report for Application No. PCT/IB2018/052412, dated Oct. 2, 2018 (7 pages).
Written Opinion of International Searching Authority for Application No. PCT/IB2018/052412, dated Oct. 2, 2018 (11 pages).

INJECTION LOCATION AND/OR DOSAGE DETERMINATION DEVICE AND SYSTEM FOR A LIQUID DRUG ADMINISTRATION DEVICE OR SYSTEM

CROSS-REFERENCE TO RELATED APPLICATIONS

This application is a U.S. National Stage of International Application No. PCT/IB2018/052412, filed Jun. 4, 2018, which claims the benefit of U.S. patent application Ser. No. 15/481,087, filed Apr. 6, 2017, both of which are incorporated herein by reference in their entireties.

FIELD OF THE INVENTION

An aspect of the present invention relates generally to embodiments of a position determination device for and method of determining and registering an injection location of self-administered liquid drug administration on a user. Furthermore, the aspect relates to calibration of such position determination devices. The position determination device may be further configured for determining a dosage activity performed by a liquid drug administration device based on obtaining at least one vibration signal.

BACKGROUND

A growing number of people have a condition involving liquid drug delivery administration where the user themselves deliver the relevant liquid drug (i.e. self-administration) by injection at an appropriate injection location or site using an injection device or the like.

The liquid drug to be delivered may be insulin but the invention is applicable to all liquid drug delivery devices where a user administers a drug on at least a somewhat regular basis, e.g. several times a day or less frequent like a number of times in a week or a month, etc., by injection into an appropriate body part.

Other examples of user-administered liquid drugs includes MS therapies with interferons and immune suppressives (e.g. like Avonex, Rebif, Copaxone etc.), different hormone therapies (growth hormone, anti-/hormone follow-up treatments to breast or prostate cancer, etc.) and injected anti-coagulants (like Heparin etc).

In such recurring self-injection regimens it is very important that the user does not inject the drug at the same location every time or too often as this may cause 'pockets' of the drug to gather under the skin, cause hard lumps, and/or cause extra fat deposits to develop as well as the onset of lipohypertrophy and/or similar skin/tissue damages (that may change the way the liquid drug is absorbed by the body at that location), and so on.

Therefore educating the user in injection techniques is often an important part of such treatment regimens and according to a current best practice in the US and the rest of the world it is recommended to change/rotate between injections locations (see e.g. Mayo Clin Procedings, September 2016; 91(9):1231-1255, Anders H. Frid, MD; Gillian Kreugel, D S N; Giorgio Grassi, MD; Serge Halimi, MD; Debbie Hicks, D S N; Laurence J. Hirsch, MD; Mike J. Smith, D S N; Regine Wellhoener, MD; Bruce W. Bode, MD; Irl B. Hirsch, MD; Sanjay Kalra, MD; Linong Ji, MD; and Kenneth W. Strauss, MD: http://www.mayoclinicproceedings.org/article/S0025-6196(16)30321-4/abstract). Furthermore, it may be recommended to inject not closer than 3 or even 1 cm (or some other distance(s)) of a previous injection location; at least within a given timeframe.

To remember and keep track of the injections, users may use certain memory systems and/or simple schematics, but compliance has been shown to usually be lowered over time, in particular for user administered injection schemes.

A typical example of patient education material is found e.g. at: http://www.cc.nih.gov/ccc/patient_education/pepubs/subq.pdf However, there is scientific evidence that a significant number of users may still forget where the last injection was made (see e.g. Diabetes Meab. 2013 October: 39(5): 445-35, Blanco M, Hernandez M T, Strauss K W, Amaya M., https://www.ncbi.nlm.nih.gov/pubmed/23886784). Furthermore, even if rotating perhaps some body locations are still used more frequently than others.

Some users may also be relatively young children, which may have a harder time sticking rigorously to a recommended rotation scheme and/or remembering it fully all the time.

Additionally, some devices furthermore provide determination of dosage activity (dosage increment, dosage decrement, and/or dosage injection) in various ways. However, there is still need for more reliable detection/registration of such dosage activity.

Patent application WO 2015/085019 discloses a device and method to encourage injection site rotation and prevent lipodystrophy from repeated injection to a body area where optical devices employing optical mouse or projection technology help locate and/or distribute injection sites within a body area and where a mobile phone app tracks injections and locations to select next injection site.

Patent application WO 2014/161952 discloses a dose logging device for a drug delivery device where a magnet is used to determine an amount of drug expelled from a reservoir for the drug delivery device.

Patent application WO 2015/136564 discloses an add-on module for monitoring and control of compliance to therapy for injectable drugs contain in pre-filled syringes having means for controlling an amount of injectable liquid and a rate of injection and means for controlling an inclination at which the injection is made with respect to skin surface in the area of injection and means for warning a user of possible anomalies during injection.

Patent application WO 2014/023763 discloses a pen-type drug injection device and add-on monitoring module for monitoring and logging dose setting and administration where the module comprises a processor and a sensor for determining the quantity of medicament that has been delivered and wherein the sensor is arranged to detect movement of a drive screw of the injection device during medicament delivery.

There is therefore a need for improved injection location handling and/or management.

It would also be a benefit to provide precise and reliable data representing actual injection location(s) and/or amount of injected liquid drug injected at a respective injection location. Additionally, it would additionally be a benefit to provide precise and reliable determination of dosage activity.

SUMMARY

It is an object to alleviate at least one or more of the above mentioned drawbacks at least to an extent.

Furthermore, it is an object to provide improved injection location handling and/or management.

Additionally, it is an object to enable precise and reliable data representing actual injection location(s) and/or amount of injected liquid drug injected at a respective injection location.

A first aspect of the invention is defined in claim 1.

According to the first aspect of the present invention is provided, a position determination device for determining and registering an injection location of a liquid drug administered on a body part of a user, where the position determination device comprises a position determination element configured to provide a position signal representing a current location of the position determination device, and one or more processing units configured to derive data representing an actual injection location on the user in response to a current location being determined by the position determination unit.

In this way, specific data is automatically obtained of where (and potentially when) one or more drug injections actually have been made. This enables improved injection location handling and/or management of the drug administration and in particular reliable data-logging of actual drug injection locations.

In some embodiments, the improved injection location handling and/or management of the drug administration includes using knowledge of previous injections locations to recommend the next appropriate injection location taking this knowledge into account—e.g. to adhere to and comply with a rotation scheme, a regimen, schedules for administering the drug, etc. and to improve drug absorption and avoid the drawbacks mentioned earlier, to actively warn a user if the user is about to use an injection location that is too close to an earlier injection location (e.g. within a given time-frame), and further on, as will be explained further in the following.

In some embodiments, the actual injection location may e.g. be calculated in the following manner: From a known or predetermined starting position, the position determination element is reset or initialised (e.g. to represent a zero-length movement vector). As the position determination device is moved, a representation of the distance moved is updated in accordance with the movement, e.g. to produce a 3D movement vector, until the position determination device is moved (e.g. via one or more anchor points as disclosed herein but not necessarily so) by the user to a final injection site whereby a position of the injection site may be determined.

In some embodiments, the one or more processing units is/are configured to derive the data representing an actual injection location on the user in response to a current location being determined by the position determination unit in response to the user administering the liquid drug using a liquid drug administration device. In this way, the action of the user specifically causing administration of the liquid drug is tied directly to obtaining the actual injection location, which increases the reliability of the obtained injection location data.

The liquid drug administration device may be of any suitable type that is used by a user or a medical professional to administer a liquid drug at an appropriate injection location on a given user. The liquid drug administration device may e.g. be an insulin administration device such as an insulin pen (simple or 'smart'), a syringe, an insulin doser, an insulin pump, etc. Alternatively, the liquid drug administration device may e.g. be a syringe or other drug delivery device for delivery of interferons, immune suppressives, hormone therapies, or other drugs or liquids.

In some embodiments, the position determination device is further configured to be (e.g. releasably) secured to a liquid drug administration device. In this way, a user can use the liquid drug administration device to administer the liquid drug as he/she normally would while obtaining reliable data of where one or more drug injections actually have been made. Furthermore, additional capabilities or 'intelligence' may readily be provided to a simple ('non-smart') liquid drug administration device such as a disposable liquid drug administration device such as certain simple insulin pens or other. This also ties movement of the liquid drug administration device directly to movement of the position determination device, which can increase accuracy and/or reliability of the injection location determination.

In some embodiments, the position determination device has a generally hollow cylindrical shape with an opening or cut-out configured to receive at least a part of a liquid drug administration device when being secured to this. This enables simple attachment to (and e.g. detachment from) the liquid drug administration device. To facilitate this further, the position determination device may e.g. have pliable walls enabling it to 'snap' onto the liquid drug administration device (and to be released therefrom again).

In some embodiments, the position determination device comprises a locking or attachment mechanism configured to releasably engage with a mating or corresponding locking or attachment mechanism of a liquid drug administration device (i.e. the locking or attachment mechanism of the position determination device is compatible with the locking or attachment mechanism of the liquid drug administration device), thereby attaching the position determination device at a predetermined location on the liquid drug administration device and/or a predetermined orientation in relation to the drug administration device. It is facilitated by such a locking or attachment mechanism that a distance from the position determination device to the needle (or another point of reference) of the drug administration device is known a priori. This avoids the need (or at least reduces it) for re-calibration every time the position determination device is attached to the drug administration device and may also increase the accuracy of the injection location determination. In some further embodiments, the locking or attachment mechanism of the position determination device corresponds to a locking or attachment mechanism of a cap of the liquid drug administration device. In this way, the position determination device may be attached or secured to the liquid drug administration device instead of the cap liquid drug administration device (using the existing locking or attachment mechanism of the liquid drug administration device normally otherwise used for attaching its cap). Additionally, the position determination device is attached or secured to the liquid drug administration device at an a priori known location.

In some further embodiments, the locking or attachment mechanism is further configured to releasably engage with a mating or corresponding locking or attachment mechanism of a cap of the liquid drug administration device thereby enabling the cap to be attached to the position determination device (even when the position determination device is attached to the drug administration device), i.e. the position determination device is (once in place) located between the drug administration device and the cap. This enables the cap still to be used for protection even when the position determination device is attached to the liquid drug administration device.

In some embodiments, the position determination device comprises a main body or housing (preferably comprising the position determination element, the one or more processing units, and other functional elements as disclosed herein) and a first separable and interchangeable part (a fitter component) wherein the first separable and interchangeable part is selected from a set of a plurality of separable and interchangeable parts, where each separable and interchangeable part of the set is configured to receive, attach with, and/or otherwise accommodate a different liquid drug administration device. In some further embodiments, the main body or housing and the first separable and interchangeable part, when joined or attached together, are configured to receive and/or accommodate a first liquid drug administration device, e.g. by enclosing the first liquid drug administration device when the main body or housing and the first separable and interchangeable part are joined or attached together. Alternatively, the first separable and interchangeable part is configured to connect with the first liquid drug administration device and to connect with the main body or housing, i.e. the first separable and interchangeable part is an intermediate way of connecting the first liquid drug administration device to the main body or housing of the position determination device. In this way, only the first separable and interchangeable part/the fitter component needs to be chosen or changed to accommodate a different type of liquid drug administration device while keeping the main body or housing of the position determination device (preferably comprising the position determination element, the one or more processing units, and other functional elements as disclosed herein) the same. The fitter component may e.g. be simple casing produced in a wide set of variations with the purpose of locking on to or connecting with the specific drug administration device (or a set or a class of specific similar drug administration devices) and providing a vehicle that the main part of the position determination device attaches to by one or more securing elements, e.g. a set of groves, magnets, or other suitable fixation mechanisms.

In some embodiments, the position determination device further comprises a wireless communications unit configured to automatically transmit the position signal or the derived data representing an actual injection location to a separate electric device (and/or the liquid drug administration device). This communication may be realized using standard such as e.g. Bluetooth, Bluetooth low energy (BLE), Near Field Communications (NFC), wifi, etc. to facilitate communication with a general (or special) purpose computation and communication device (e.g. a smartphone, a tablet, a laptop, a computer, etc.).

In some embodiments, the position determination device is configured to derive the data representing an actual injection location one the user in response to response to a current location being determined by the position determination unit in response an actual action of the user activating the liquid drug administration device to administer the liquid drug triggers deriving the data representing an actual injection location. In this way, precise registration of the injection location is provided as the moment of deriving the data is tied directly to the actual drug administration.

In some embodiments, a mechanical or remote sensor is attached directly to, or attached in connection with, an activation button or element of the liquid drug administration device where the mechanical or remote sensor is configured to detect movement or activation of the activation button or element of the liquid drug administration device. In some alternative embodiments, a sensor is configured to detect activation of the activation button or element by other ways than movement.

A mechanical sensor may e.g. be physically attached or parallel to the activation button or element. A remote sensor could measure the distance to the activation button or element and determine any changes in the activation button or element's position in relation to the position determination device.

In some embodiments, the position determination device further comprises a sound sensor configured to register one or more distinct sounds caused by the drug administration device when operated by a user to release or administer a drug dosage as an actual action of the user and wherein the position determination device is configured to trigger deriving the data representing an actual injection location in response to registering and identifying the one or more distinct sounds. Such distinct sounds are common e.g. among insulin administration devices and other types of liquid drug administration devices to provide user feedback and/or allow users with impaired sight to hear when the dosage is released. Alternatively, or in addition, the position determination device further comprises a vibration sensor (e.g. a (3 axes) accelerometer, a (3 axes) gyrometer, a six degree of freedom (DoF) inertial measurement unit (IMU), or other movement/vibration detector) configured to register one or more distinct vibrations caused by a user operating the liquid drug administration device to release a drug dosage as an actual action of the user and wherein the position determination device is configured to trigger deriving the data representing an actual injection location in response to registering and identifying the one or more distinct vibrations/vibration signals or signals derived therefrom. Accordingly, registration and identification of sound and/or vibrations signals or profiles may be used to reliably capture the actual release of the liquid drug by the liquid drug administration device as disclosed herein. Predetermined sound and/or vibration profiles (e.g. for several different liquid drug administration devices) may e.g. be stored in a suitable memory and/or storage (e.g. of the position determination device or an external device) and be used to compare with obtained sound and/or vibration signals to determine whether and when the liquid drug is actually released or administered.

In some embodiments, the position determination device further comprises
- a memory and/or storage comprising data representing at least one previous injection location,
- at least one indicator element, configured to signal to the user
  - that a current location of the position determination device, as determined by the position determination element, is at a location where it is acceptable and/or advisable to perform an injection taking into account at least the data representing at least one previous injection location, and/or
  - that a current location of the position determination device, as determined by the position determination element, is at a location where it is not acceptable and/or not advisable to perform an injection taking into account at least the data representing at least one previous injection location.

Accordingly, improved injection location handling and/or management of the drug administration is provided that includes using knowledge of previous injections locations to recommend the next appropriate injection location taking this knowledge into account—e.g. to adhere to and comply with a rotation scheme, a regimen, schedules for administering the drug, etc. and to improve drug absorption and avoid the drawbacks mentioned earlier, to actively warn a user if the user is about to use an injection location that is too close to an earlier injection location (e.g. within a given time-frame), and further on.

Alternatively, the data representing at least one previous injection location is stored in a memory and/or storage of an external device and the position determination device may then simple receive a (ok and/or not ok) signal from the external device.

An indicator element may e.g. be or comprise one or more of a light emitter, an LED, a sound emitter, vibration or haptic unit, graphical element(s) as part of a graphical user interface displayed on a display or similar, etc. or any other suitable emitter or indicator capable of signaling suitable indications to the user.

In some embodiments, the position determination element comprises at least one gyroscope (may also be referred to a gyrometer) and/or at least one accelerometer configured to provide the position signal representing a current location of the position determination device. In some further embodiments, the position determination element comprises three gyroscopes and three accelerometers aligned orthogonally in relation to three primary axes of the device frame, e.g. also referred to as a six degree of freedom (DoF) inertial measurement unit (IMU) providing signals indicative of translational movement in three perpendicular axes (surge, heave, sway) and rotational movement about the same three perpendicular axes (roll, pitch, yaw). Such setups allow the position determination device to capture accelerations and rotations for a device being moved freely in 3D space.

In some embodiments, the position determination element comprises one or more elements adding further reference point(s) and parameter(s) for determining the injection location. In some such embodiments, the position determination element comprises at least one magnetometer or magnetism measuring element configured to provide the position signal representing a current location of the position determination device by measuring a relative drop in signal strengths along respective axes of the magnetometer or magnetism measuring element in relation to a permanent or electromagnet source that is kept stationary at least during determination of the injection location. In some other such embodiments, the position determination element comprises at least one sound transceiver configured to provide the position signal representing a current location of the position determination device by emitting a predetermined sound signal that is reflected by a sound reflecting source, that is kept stationary at least during determination of the injection location, and measuring a period of time from emitting the predetermined sound signal until the reflected signal is received by the at least one sound transceiver. In some further such embodiments, the position determination element comprises at least one sound sensor configured to provide the position signal representing a current location of the position determination device by measuring a sound level of a predetermined sound signal emitted by a sound emitting source that is kept stationary at least during determination of the injection location. In some yet other such embodiments, the position determination element comprises at least one light sensor configured to provide the position signal representing a current location of the position determination device by measuring an angle of a predetermined light signal being emitting by a light source and reflected by a reflector having a material with predetermined reflective properties, the light source being configured to pivot in different directions, where the at least one light sensor, the light source, and the reflector are kept stationary at least during determination of the injection location. In some yet further such embodiments, the position determination element comprises at least one radio signal sensor configured to provide the position signal representing a current location of the position determination device by measuring a signal strength of a predetermined radio signal emitted by a radio signal source, that is kept stationary at least during determination of the injection location, or by measuring a period of time from emitting a predetermined radio signal by a radio signal source, that is kept stationary at least during determination of the injection location, until the emitted radio signal is received by the at least one radio signal sensor.

In some embodiments, the one or more position determination elements comprise a combination of the exemplary embodiments comprising one or more elements adding further reference point(s) and parameter(s) for determining the injection location given above and as disclosed herein. This will add further reference point(s) and parameter(s) for determining the injection location thereby further increasing the quality and/or reliability thereof.

In some embodiments, the permanent or electromagnet source, the sound reflecting source, the sound emitting source, the light source, the reflector, and/or the radio signal source is located in a cap of a liquid drug administration device. In this way, the respective element(s) (to be kept stationary at least during determination of the injection location), are readily available at the time of injection. The element(s) (e.g. the cap) may e.g. simply be placed on a table or other during determination of injection location thereby providing a fixed reference point for use in determination of the injection location.

In some embodiments, the position determination device is further configured to register an actual amount of administered liquid drug and/or a time-stamp when or in connection with deriving data representing an actual injection location. In this way, an accurate data or diary log may automatically be provided that improves daily diabetes administration for the user and/or as well as providing data for improving treatment by healthcare professionals, for academic use, etc.

In some embodiments, the position determination device further comprises an image sensor or other sensor element configured to detect an amount of liquid drug being administered by the liquid drug administration device. In this way, dosage data may be collected (and communicated further on) by the position determination device in situations where a liquid drug administration device otherwise does not support this. In some embodiments, this is achieved by using an image sensor that is e.g. hand held by the user or mounted on e.g. a pair of glasses or elsewhere on the user. The image produced by the image sensor would then e.g. be digitally processed to identify the liquid drug administration device, an injection region or location, and a location of the liquid drug administration device in relation to the injection region or location. This may be achieved by using any suitable image processing techniques such as but not limited to e.g. edge detection, ANN (artificial neural networks), DNN (deep neural networks), or some combination or derivation hereof. In some embodiments, image recognition may be used to augment or supplement the position determination techniques described herein. The image recognition could e.g. add a second source of data to the movement based and/or other detector based technique(s) disclosed herein thus improving precision and/or reliability further. In other embodiments, image recognition could be used to determine actual starting points of the movement of hand and drug administration device thus reducing the need for fixed calibration.

In some embodiments (e.g. in combination with registering release or administering a drug dosage as described above and disclosed herein), the position determination device further comprises a sound sensor configured to register one or more distinct sounds caused by a user operating the liquid drug administration device to increase and/or decrease a drug dosage as one or more actual actions of the user and wherein the position determination device is configured to derive an amount of liquid drug being administered by the liquid drug administration device in response to registering and identifying the one or more distinct sounds, and/or a vibration sensor (e.g. a (3 axes) accelerometer, a (3 axes) gyrometer, a six DoF IMU, or other movement/vibration detector) configured to register one or more distinct vibrations caused by a user operating the liquid drug administration device to increase and/or decrease a drug dosage as one or more actual actions of the user and wherein the position determination device is configured to detect an amount of liquid drug being administered by the liquid drug administration device in response to registering and identifying the one or more distinct vibrations.

Detection of sounds/vibration may e.g. be done as disclosed herein.

In some embodiments, the position determination device is further configured to register a starting position in response to the user moving the position determination device to a pre-determined starting position, register a location of an anchor position in response to the position determination unit determining the movement from the starting position to the anchor position, register a location of the actual injection location in response to the position determination unit determining the movement from the anchor position to the injection location.

In some embodiments, the position determination device is further configured to recommend the anchor position and/or recommend the location of the actual injection location in response to stored and/or received data representing a rotation schema (e.g. stored as data in the position determination device or in a separate electric device and being received therefrom) taking into account data representing one or more previously registered actual injection locations.

In some embodiments, the position determination device is further configured to register a starting position when the user has moved the position determination device to a starting position, if used, register a region in connection with the starting position defining a region suitable for receiving injections, register one or more anchor points, by determining their relative position in relation to the starting position, and for each anchor point registering a region defining a region associated with the given anchor point being suitable for receiving injections.

In some embodiments, the liquid drug is one selected from the group consisting of: insulin, a drug for multiple sclerosis therapy with interferons and immune suppressives (e.g. like Avonex, Rebif, Copaxone etc.), a drug for hormone therapy, a drug for growth hormone therapy, and a drug for hormone/anti-hormone follow-up treatment to breast or prostate cancer.

In some embodiments, the position determination device is integrated with a liquid drug administration device and wherein the derived data or position signal representing an actual injection location is transferred to at least another electric element of the liquid drug administration device.

In some embodiments, the position determination device is for determining and registering an injection location of self-administered liquid drug administration on a user.

In some embodiments, the position determination device is for determining and registering an injection location of administered liquid drug administration on a user administered by a medical professional.

According to some embodiments, the position determination device as disclosed herein may be used in connection with a dock or similar to recharge and/or transfer information and/or data as generally known.

According to some embodiments, the position determination device (and embodiments thereof) as disclosed herein is also a dosage determination device (and embodiments thereof), i.e. has the elements and functionality thereof, as disclosed herein. Accordingly and/or additionally, the position determination device comprises one or more of the elements and/functionality of the dosage determination device as disclosed herein. In particular and as an example, a position determination element (used to determine location) of the position determination device may comprise or also be a vibration determination element (used to determine a dosage activity) as disclosed herein.

According to a second aspect is provided a position determination system for determining and registering an injection location of a liquid drug administered on a body part of a user, wherein the position determination system comprises a position determination element configured to provide a position signal representing a current location of the position determination device, and one or more processing units configured to derive data representing an actual injection location on the user in response to a current location being determined by the position determination unit.

In some embodiments, the position determination system further comprises a liquid drug administration device and wherein the one or more processing units are configured to derive the data representing an actual injection location based on a current location determined by the position determination unit in response to the user administering the liquid drug using the liquid drug administration device.

In some further embodiments, one or more of the elements of the system as described above correspond(s) to one or more similar elements of the position determination device or one or more similar elements as described in connection with the position determination device as disclosed herein.

Another aspect of the present invention is a use of a position determination device as disclosed herein (and combinations thereof) or the position determination system as disclosed herein to register one or more locations of actual injection locations.

According to another aspect of the present invention is provided an electronic device configured to collect and/or obtain data representing a history of actual injection locations (e.g. obtained or provided by a position determination device as disclosed herein) where one or more processing units of the device is/are configured to display a graphical representation on a display of at least a part of the data representing a history of actual injection locations as a 'heat map' or similar where the individual values (location e.g. together with further relevant information like time of injection, actual amount of injected liquid drug, etc.) are represented and/or displayed as colors according to a color scheme superimposed on a picture or a graphic representation of the overall injection area(s), e.g. like the torso, the thighs, upper arms, or what other injection area the user has defined, etc. The values may e.g. be stored in a matrix data structure and/or any other suitable data structure. The color scheme may e.g. be one from green to red where a given injection location is marked yellow if it was taken in (too) close proximity (e.g. within 1 or 3 cm, or as chosen by the user) to one another injection location made within a predetermined time (e.g. a week or other timeframe as e.g. determined by the user), and red if it is in (too) close proximity to 2 or more injection locations, and green in all other cases.

The heatmap may be displayed to a user prior to the user performing an injection thus enabling the user to check an intended injection location in relation to previous injection locations.

In a recommendation mode, the device itself may show status of injection locations based on the same color scheme or recommend locations based on the chosen rotation principles and e.g. assessment of possible lipohypertrophy by medical professionals thereby guiding the user to a suitable injection site. In some further embodiments, this involves showing injection history, areas to avoid because of lipohypertrophy, and/or areas to inject in. The aspect of displaying previous injection locations like this may be used independently of the described aspects and embodiments of the position determination device as disclosed herein although they together work especially well.

A further aspect of the invention is defined in claim 1. According to this further aspect of the present invention is provided a dosage determination device for determining a dosage activity performed by a liquid drug administration device, the dosage determination device being configured to
  obtain at least one vibration signal from a vibration determination element (e.g. comprised by the dosage determination device or alternatively an external device or system), the vibration determination element being configured to obtain the at least one vibration signal in response to registering vibration of the liquid drug administration device,
wherein the dosage determination device further comprises one or more processing units configured to
  provide a first processed signal by deriving a derivative or a second order derivative on the basis of at least a part of the at least one vibration signal,
  determine a number of local extrema in the first processed signal resulting in a number of determined local extrema, and
  processing the number of determined local extrema by matching against predetermined patterns of groups of local extrema, each group of predetermined local extrema representing a particular associated dosage activity, thereby determining whether at least one dosage activity (dosage increment, dosage decrement, and/or dosage injection) is indicated to be present in the at least one vibration signal.

In this way, more reliable determination of dosage activity is provided.

The number of processed determined local extrema may e.g. be done as is disclosed herein.

According to some embodiments, the vibration determination element comprises at least one gyrometer and/or at least one accelerometer and wherein the at least one vibration signal obtained by the dosage determination device comprises at least one gyrometer vibration signal and/or at least one accelerometer vibration signal.

According to some embodiments, the vibration determination element is a six degree of freedom inertial measurement unit providing six signals respectively indicative of translational movement along three predetermined perpendicular axes and of rotational movement about the three predetermined perpendicular axes, whereby the least one vibration signal comprises three orthogonal gyrometer vibration signals and three orthogonal accelerometer vibration signals.

According to some embodiments, the at least one vibration signal comprises a plurality of vibration signals and wherein the one or more processing units are further configured to
  derive a combined signal on the basis of at least some, e.g. all, of the plurality of vibration signals, and
  provide the first processed signal by deriving a derivative or a second order derivative of the combined signal instead of on the basis of at least a part of the at least one vibration signal.

According to some embodiments, the one or more processing units are configured to derive the combined signal by subtracting an amplitude of one of the plurality of vibration signals (e.g. primary or most significant axis) by an amplitude of at least one other of the plurality of vibration signals (e.g. subtracting by the sum of the other (non-primary) axis signals).

According to some embodiments, the at least one vibration signal comprises a plurality of gyrometer vibration signals and a plurality of accelerometer vibration signals and wherein the one or more processing units are configured to
  derive a first combined signal (i.e. a combined gyrometer vibration signal) on the basis of the plurality of gyrometer vibration signals, and
  derive a second combined signal (i.e. a combined accelerometer vibration signal) on the basis of the plurality of accelerometer vibration signals.

According to some embodiments, the one or more processing units are configured to derive a third combined signal on the basis of the first combined signal and the second combined signal.

According to some embodiments, the one or more processing units are configured to derive the third combined signal by subtracting the second combined signal from the first combined signal.

According to some embodiments, the dosage determination device is configured to
  obtain at least one sound signal from at least one sound sensor (e.g. comprised by the dosage determination device or alternatively an external device or system) configured to register one or more distinct sounds caused by the drug administration device when operated by a user to perform the dosage activity, and
  provide the first processed signal on the basis of at least a part of the at least one sound signal instead or in addition to at least a part of the at least one vibration signal.

According to some embodiments, the dosage determination device is configured to
  determine whether at least one dosage activity (dosage increment, dosage decrement, and/or dosage injection) is indicated to be present in the at least one vibration signal, determine whether at least one dosage activity (dosage increment, dosage decrement, and/or dosage injection) is indicated to be present in the least one sound signal, and deciding that at least one dosage activity is determined only if the at least one dosage activity is determined to be present in both the at least one vibration signal and the least one sound signal.

This may e.g. be done for a number of signals—e.g. for a gyrometer vibration signal, a accelerometer vibration signal, and a sound signal and deciding that a dosage activity is determined to be present if all (or a majority) has determined this individually.

In some embodiments, a first and/or a second combined signal is processed for the presence of dosage activity e.g. together with processing of a sound signal also processed for the presence of dosage activity and deciding that a dosage activity is determined to be present if all (or a majority) has determined this individually.

Definitions

All headings and sub-headings are used herein for convenience only and should not be constructed as limiting the invention in any way.

The use of any and all examples, or exemplary language provided herein, is intended merely to better illuminate the invention and does not pose a limitation on the scope of the invention unless otherwise claimed. No language in the specification should be construed as indicating any non-claimed element as essential to the practice of the invention.

This invention includes all modifications and equivalents of the subject matter recited in the claims appended hereto as permitted by applicable law.

BRIEF DESCRIPTION OF THE DRAWINGS

as illustrated in FIG. 1;

as shown in FIGS. 1 to 3b, 8 to 9, and 12, and embodiments thereof;

as shown in FIGS. 1 to 3b, 8 to 9, and 12, and embodiments thereof;

FIG. 8 schematically illustrates an embodiment of a locking mechanism for attaching an embodiment of a position determination device to a drug administration device;

DETAILED DESCRIPTION

Various aspects and embodiments of a position determination device for and methods of determining and registering an injection location of administered liquid drug administration on a user and calibration of such position determination devices as disclosed herein will now be described with reference to the figures. Additionally, various aspects and embodiments of a dosage determination device for determining a dosage activity performed by a liquid drug administration device as disclosed herein will also be described with reference to the figures.

When/if relative expressions such as "upper" and "lower", "right" and "left", "horizontal" and "vertical", "clockwise" and "counter clockwise" or similar are used in the following terms, these refer to the appended figures and not necessarily to an actual situation of use. The shown figures are schematic representations for which reason the configuration of the different structures as well as their relative dimensions are intended to serve illustrative purposes only.

Figure 2A:
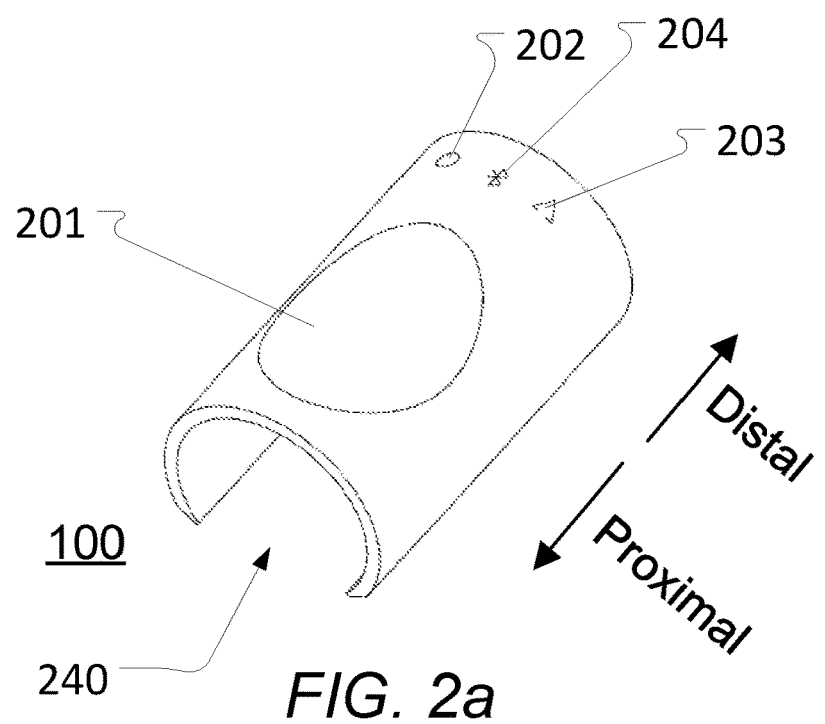
FIGS. 2a-2d schematically illustrate different views of one exemplary embodiment of a position determination device e.g.
Figure 3A:
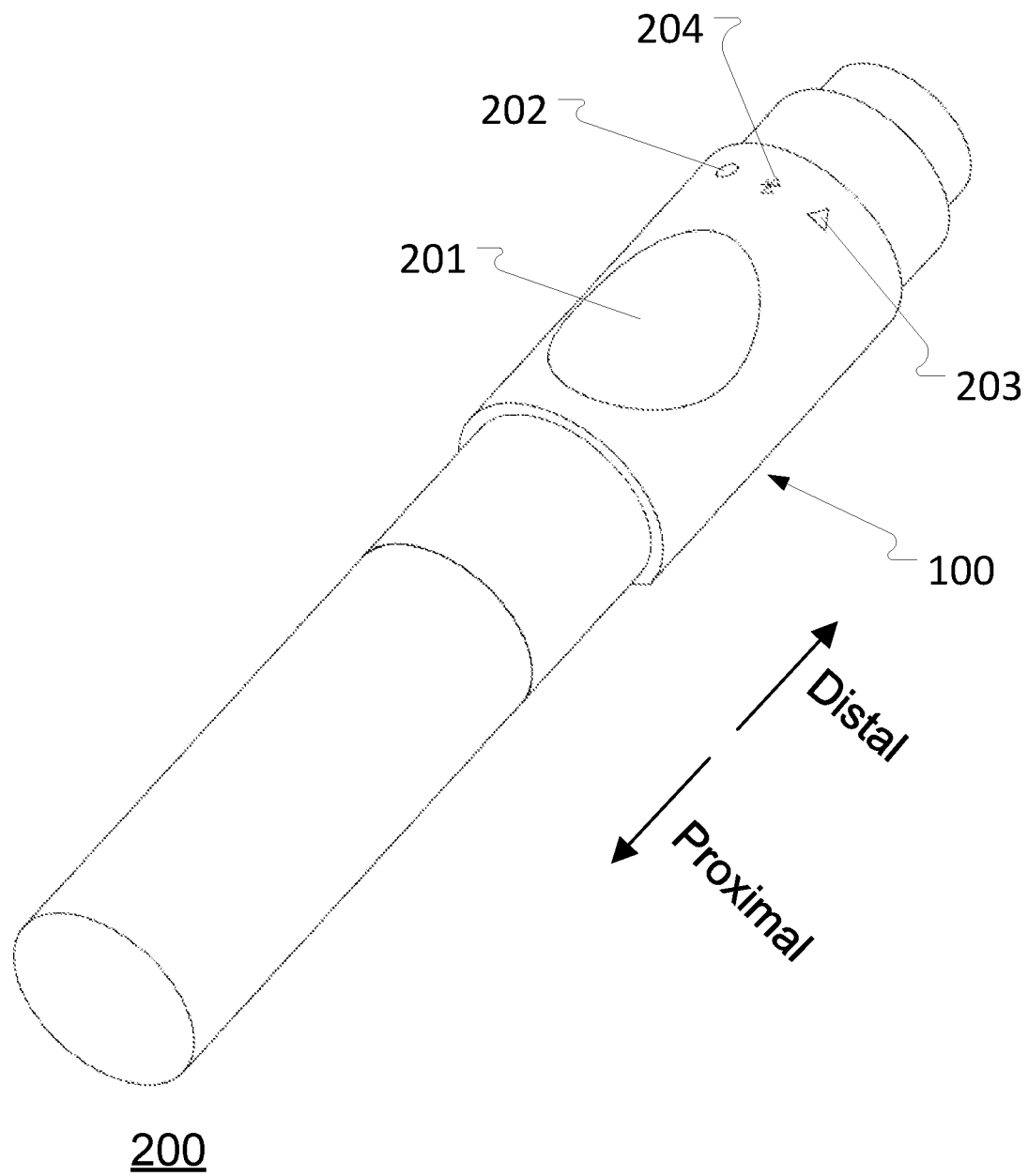
FIG. 3a schematically illustrates a perspective view of the position determination device of FIGS. 2a-2d being secured to a liquid drug administration device.
Figure 3B:
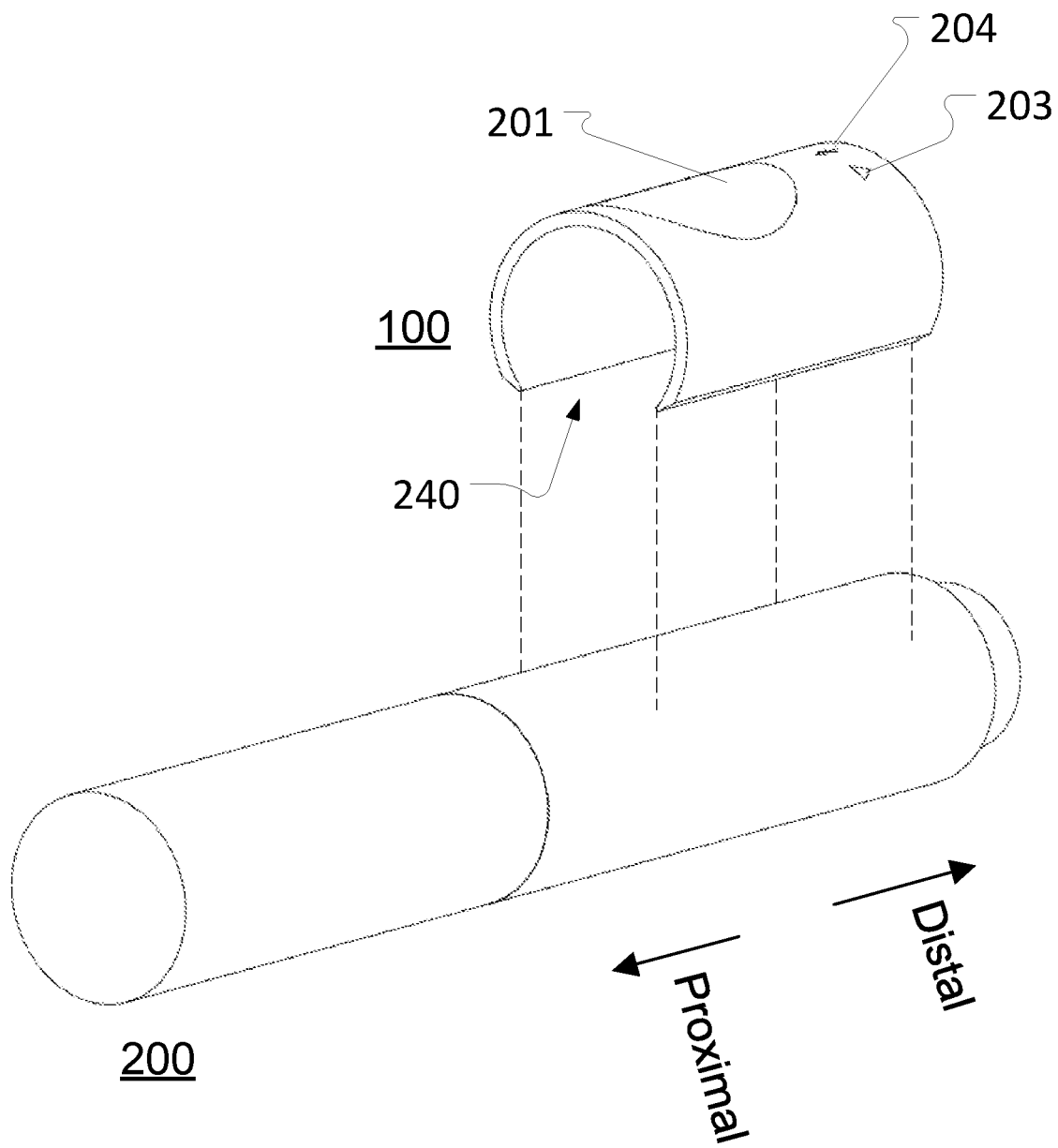
FIG. 3b schematically illustrates a perspective view of the position determination device and the liquid drug administration device of FIG. 3a before the position determination device is secured to the liquid drug administration device.

In that context, it may be convenient to define that the term "proximal direction" in the appended figures is meant to refer to the direction of the position determination device (and its associated or integrated liquid drug administration device) that normally, during use, would point towards an injection element of the liquid drug administration device, as depicted e.g. in FIGS. 2a and 3a-3b, whereas the term "distal direction" is meant to refer to a direction parallel and opposite to the proximal direction.

Figure 1:
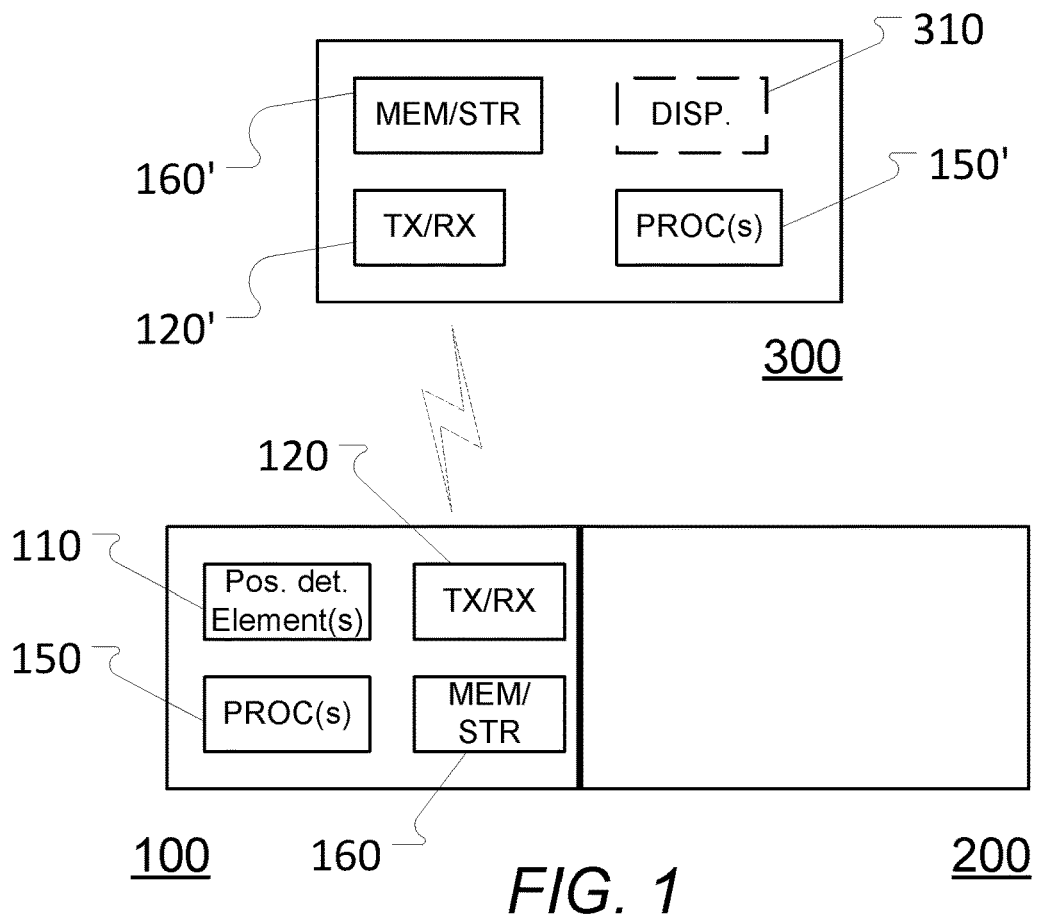
FIG. 1 illustrates a schematic block diagram of embodiments of a position determination device.

FIG. 1 illustrates a schematic block diagram of embodiments of a position determination device.

Shown is one embodiment of a position determination device 100 and a liquid drug administration device 200. The position determination device 100 may e.g. be integrated with the liquid drug administration device 200 or alternatively be (e.g. releasably) attached or secured to the liquid drug administration device 200, e.g. as shown and explained further in connection with FIGS. 3a-3b, 8-9, 12a-12b, or alternatively of another type.

The liquid drug administration device 200 may be of any suitable type that is used by a user or a medical professional to administer a liquid drug at an appropriate injection location on a given user. The liquid drug administration device 200 may e.g. be an insulin administration device such as an insulin pen (simple or 'smart'), a syringe, an insulin doser, an insulin pump, etc. Alternatively, the liquid drug administration device may e.g. be a syringe for delivery of interferons, immune suppressives, hormone therapies, or other drugs or liquids.

The position determination device 100 comprises one or more position determination elements 110 and in this particular and other embodiments, one or more processing units 150, at least one digital memory and/or storage 160, and at least one communications unit 120, preferably one or more standardized wireless communications units e.g. like Wi-Fi, Bluetooth, NFC, etc. communications units. The position determination element(s) may also double in function as a vibration determination element as disclosed herein.

If the position determination device 100 is integrated with the liquid drug administration device 200 they may share one or more elements, such as the processing unit(s), the digital memory/storage, and/or the communication unit(s).

Further shown is a separate electric device 300 comprising its own one or more processing units 150', at least one digital memory and/or storage 160', at least one communications unit 120', and optionally a display 310.

Preferably, the position determination device 100 (and/or the liquid drug administration device 200) may wirelessly communicate or exchange data and information with the separate electric device 300.

The separate electric device 300 may e.g. be a mobile communications and/or computation device such as a smartphone, a tablet, a laptop or PC, etc. or a separate dedicated special purpose device, such as a data-logger or the like.

The position determination device 100 is for determining and registering an injection location of (e.g. self-administered) liquid drug administration on a body part of a user as will be explained in the following and as disclosed herein.

According to an aspect of the present invention, the position determination element 110 is configured to provide, during use, a position signal representing a current location of the position determination device 100 and the one or more processing units 150 is/are configured to derive, during use, data representing an actual injection location on the user in response to a current location being determined by the position determination unit 110. Alternatively (or in addition), the position determination device 100 is configured to transmit, via the communications unit 120, the position signal representing directly or indirectly the current location to the separate electric device 300, the liquid drug administration device 200, and/or another device instead of deriving the data representing an actual injection location. The derivation of the data may e.g. then be performed by the receiving device.

According to a further aspect of the present invention, the position determination device 100 may be attached or secured and (releasably) locked in relation to the drug administration device 200 with the use of a locking mechanism according to various embodiments (see e.g. 701 in FIGS. 8 and 9 for one embodiment) at a predetermined location on and/or predetermined orientation in relation to the drug administration device 200. In this way, it is ensured by such a locking mechanism that a distance from the position determination device 100 to the needle of the drug administration device 200 is always known a priori. This avoids (or at least reduces) the need for re-calibration every time the position determination device 100 is attached to the drug administration device 200.

In some further embodiments, the position determination device 100 attaches to the drug administration device 200 like a cap of the drug administration device 200 normally would when the position determination device 100 is not present, i.e. the locking mechanism of the position determination device 100 corresponds to the locking mechanism of the cap in that they will be the same or at least similar or compatible. This ensures that the position determination device 100 can be attached or secured to the drug administration device 100 in a reliable way, since the locking mechanism position determination device 100 is a 'copy' of or at least being corresponding to the locking mechanism of the cap.

Figure 8:
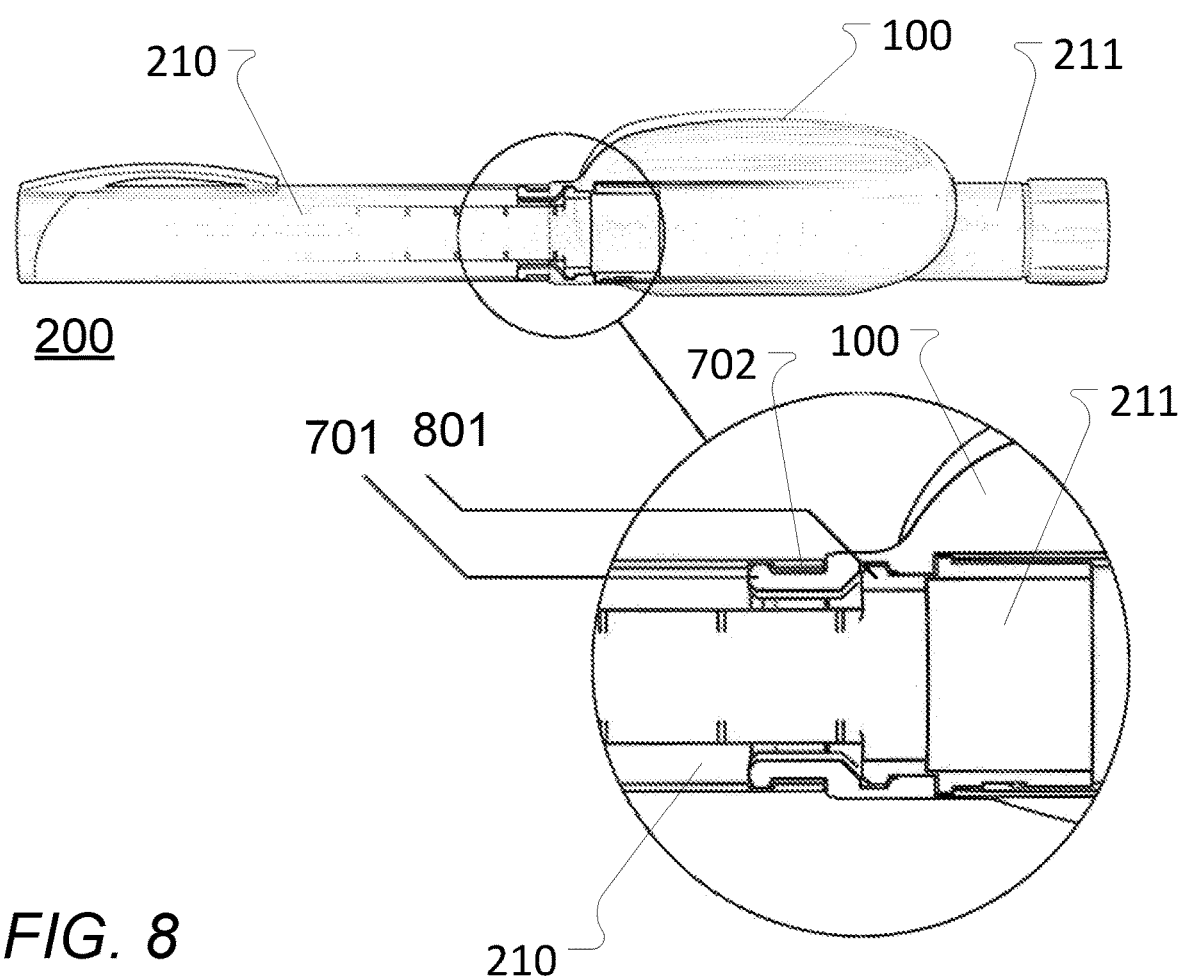

In some further embodiments, the position determination device 100 is further configured to allow the cap of the drug administration device 200 to be attached to the position determination device 100 rather than directly to the drug administration device 200 itself when the position determination device 100 is attached or secured to the drug administration device 200 (see e.g. 702 in FIGS. 8 and 9). This ensures that the cap may still be attached thereby protecting the relevant parts of the drug administration device 200 in a usual way.

The actual injection location may e.g. be calculated in the following manner: From a known or predetermined starting position, the position determination element 110 is reset or initialised (e.g. to represent a zero-length movement vector). As the position determination device 100 is moved, the position determination element 110 update its internal representation of the distance moved e.g. to produce a 3D movement vector. When the position determination device 100 is moved to an anchor point, this movement vector is compared to the calibrated vectors to determine which anchor point the position determination device 100 is at. In addition, data from the position determination element 110 may e.g. be used to determine the relative position in relation to the torso or the limb where the anchor point is located. The border of the injection area around the anchor points is calibrated e.g. as described in connection with FIG. 6. Using the calibrated area, the anchor position, the starting position, and the internal movement vector, the exact position of the injection site may be determined when the position determination element 100 (and e.g. the liquid drug administration device 200 as attached or integrated) is moved by the user to a final injection site.

In this way, specific data is obtained of where (and e.g. when) one or more drug injections actually have been made. This enables improved injection location handling and/or self-management of the drug administration including e.g. using knowledge of previous injections locations to recommend the next appropriate injection location taking this knowledge into account—e.g. to adhere to and comply with a rotation scheme, a regimen, schedules for administering the drug, etc. and to improve drug absorption and avoid the drawbacks mentioned earlier, to actively warn a user if the user is about to use an injection location that is too close to an earlier injection location (e.g. within a given time-frame), and further on, as will be explained further in the following.

Depending on specific circumstances, the location signal or signals as obtained by the one or more position determination elements 110 may comprise a certain amount of (background) noise. In some embodiments, the position determination device 100 comprises elements to at least reduce or mitigate such noise. According to some such embodiments, the one or more position determination elements 110 comprises at least one accelerometer or other suitable movement detection element where movement sensor data or one or more movement sensor signals is used to determine whether the position determination device 100 is stationary or in movement (e.g. in relation to a background measurement of standard gravity g).

For portions of the obtained signal that is determined to reflect a movement of the position determination device 100, the signal will contain first an acceleration (indicating a start of the movement) and subsequently a deceleration (indicating an end of the movement) back to a stationary position. This may be compared against a priori knowledge of human arm movement to fit the noisy signal to a noise-free curve and thereby extract a signal with at least reduced noise that then may be used for determination of the injection location as disclosed herein.

In some embodiments, the position determination device 100 may automatically transmit, using the wireless communications unit 120, the derived data representing an actual injection location (or alternatively a signal representing the actual injection location as obtained by the one or more position determination elements 110) to the separate electric device 300 and/or the liquid drug administration device 200. In this way, the data relating to actual injection is readily made available and may be used for various purposes e.g. as disclosed herein. Alternatively, the position determination device 100 may automatically transmit, using the wireless communications unit 120, a signal representing the actual injection location or a signal representing current location or subsequent current locations as obtained by the one or more position determination elements 110 to the separate electric device 300 and/or the liquid drug administration device 200. In this way, the separate electric device 300 and/or the liquid drug administration device 200 can derive the data representing an actual injection location.

In some embodiments, the data representing an actual injection location is derived in response to the user administering the liquid drug using the liquid drug administration device 200. This may in some embodiments be an actual action of the user actually activating the liquid drug administration device 200 to administer the liquid drug that triggers deriving the data representing an actual injection location e.g. as disclosed herein.

In some embodiments, the position determination device 100 may also comprise at least one indicator element (see e.g. 202, 203, and 204 in FIGS. 2a-3b and 9).

The at least one indicator element (e.g. light, LED, sound emitter, etc.) may be configured to signal to the user, during use, that a current location of the position determination device 100, as determined by the position determination element 110, is at a location where it is acceptable or advisable to perform an injection taking into account at least the data representing at least one previous injection location.

The at least one indicator element may alternatively or in addition be configured to signal to the user, during use, that the current location of the position determination device 100, as determined by the position determination element 110, is at a location where it is not acceptable or advisable to perform an injection taking into account at least the data representing at least one previous injection location.

In addition or as an alternative, the separate electric device 300 and/or the liquid drug administration device 200 may comprise at least indicator element performing the same function(s).

One or more of the at least one indicator elements may also be graphical elements as part of a graphical user interface displayed on a display.

The one or more position determination elements 110 may e.g. comprise at least one gyroscope and/or at least one accelerometer (e.g. a six DoF IMU) to determine a location, e.g. in a relative way using fixed known/calibrated positions, as will be explained further in the following and as disclosed herein.

Alternatively, other types of position determination elements may be used e.g. including absolute measurement elements. In such embodiments, the one or more position determination elements 110 may e.g. comprise a magnetometer or similar configured to derive the location in relation to a permanent or electromagnet source that is kept stationary at least during determination of the injection location. The location can thereby be derived by measuring a relative drop in signal strengths along three axes of the magnetometer or similar thereby given a distance and angle to the magnet source.

Alternatively, the one or more position determination elements 110 may e.g. comprise a sound sensor for deriving a distance to a stationary (at least during determination of the injection location) sound emitting source by measuring a level of (e.g. ultra) sound. The distance in these embodiments may e.g. be derived by synchronizing clocks before the measurements or activating the sound source at fixed intervals and measuring the delay between the sound being emitted and being received thereby deriving a distance between the sound sensor and the stationary sound source. The stationary source (then not being sound emitting) may also comprise a material with predetermined reflective properties and measure the time for the signal to travel back and forth enabling deriving a distance between them.

Furthermore, the one or more position determination elements 110 may e.g. comprise a light sensor, a reflector or the like, and light source similar to the sound sensor setup, but using visible, infrared, or ultraviolet light instead of sound waves as the property being measured. In such a setup, the light source, the reflector or similar, and the light sensor may be arranged at fixed positions in relation to each other where the light source pivots to allow emitting light at various angles in relation to the light sensor. By measuring the angle at which light is returned by the material of the reflector (having predetermined reflective properties), the distance can be derived e.g. using standard techniques for IR/UV distance measurements as readily known.

Additionally, the one or more position determination elements 110 may e.g. comprise a radio signal source and sensor to derive the distance between the two e.g. by measuring the relative signal strength or by measuring the time for a signal to travel between the source and the sensor. In some embodiments, the respective source may e.g. be the separate electric device 300 or alternatively, the respective source may be separate from both the separate electric device 300 and the position determination device 100.

In some expedient embodiments, the stationary (at least during determination of the injection location) element may be located or integrated e.g. in the cap of the liquid drug administration device 200 thereby allowing the stationary element to readily be available at the time of injection. The stationary element (e.g. the cap) may e.g. simply be placed on a table or other during determination of injection location thereby providing a fixed reference point for use in determination of the injection location.

In some embodiments, the one or more position determination elements 110 comprises a combination of the exemplary embodiments given above and as disclosed herein. This will add further reference point(s) and parameter(s) for determining the injection location thereby further increasing the quality and/or reliability thereof.

In some embodiments, the position determination device 100 may also be a dosage determination device as disclosed herein or at least comprises one or more (depending on specific embodiments) corresponding elements and/or functionality as disclosed herein.

FIGS. 2a-2d schematically illustrate different views of one exemplary embodiment of a position determination device e.g. as illustrated in FIG. 1.

Shown in FIG. 2a is one exemplary embodiment of a position determination device 100 corresponding, in function at least, to embodiments already described in connection with FIG. 1 and as disclosed herein. This particular embodiment is of a position determination device 100 that is configured to be (releasably) attached or secured, during use, to a liquid drug administration device, e.g. like 200 described in connection with FIG. 1 and elsewhere.

The position determination device 100 may e.g. be configured to be secured to the liquid drug administration device using one or more suitable attachment elements or similar (not shown; see e.g. 701 in FIGS. 8 and 9 for one example).

Alternatively, the position determination device 100 may be configured to be (releasably) secured to the liquid drug administration device 200 due to its particular shape, e.g. such as shown in this figure and explained further in the following in connection with FIGS. 3a and 3b.

In this and corresponding embodiments, the position determination device 100 comprises one activation or operation button or similar 201 and at least one indicator element (here three as an example) 202, 203, 204 such as one or more lights, LEDs, etc., and/or one or more sound emitters used to signal the user of various indications, information, status, etc.

In the shown embodiment, the position determination device 100 comprises a confirmation light or LED 202, a warning light or LED 203, and a wireless communications connection light or LED 204.

The confirmation light or LED 202 may, as disclosed herein, indicate when a given position is ok for drug injection, while the warning light or LED 203 may indicate when a given position is not ok. The connection light or LED 204 may indicate when a wireless connection is established to a separate electric device (e.g. like 300 in FIGS. 1 and 7) and/or a liquid drug administration device (e.g. like 200 in FIGS. 1, 3, 8, and 9).

It should be noted, that the functions of two or more lights or LEDs could be done by fewer lights or LEDs, e.g. only a single one. As an example, one multi-colored light or LED could be e.g. green for confirmation and red for warning. In addition or as alternatives, the indications could also be audible e.g. using one or more sound emitters or the indications of whether a position is ok or not ok could be done by vibration or a set of different vibrations e.g. using one or more haptic elements.

The indications could also be given on a separate electric device (e.g. like 300 in FIGS. 1 and 7) e.g. in an app or program running on a smartphone, tablet, laptop, PC, etc. and/or on a liquid drug administration device (e.g. like 200 in FIGS. 1, 3, 8, and 9) instead or in duplication.

Also indicated in FIG. 2a is a proximal and a distal direction. The proximal direction is a direction generally towards the end of the position determination device 100 that normally would be closest to the injection element of a liquid drug administration device (see e.g. 200 in FIGS. 1, 3a-3b, 8, and 9) that the position determination device 100 is secured to while the distal direction is parallel and opposite to the proximal direction.

It should be noted, that the orientation of the position determination device 100 when secured to the liquid drug administration device in certain embodiments may not be significant. The shown embodiment of the position determination device 100 could e.g. be rotated about its central axis on the liquid drug administration device and it could e.g. also be flipped or turned 180° (so the otherwise distal end of the position determination device 100 now would be in the proximal direction of the liquid drug administration device) while still working.

Figure 2B:
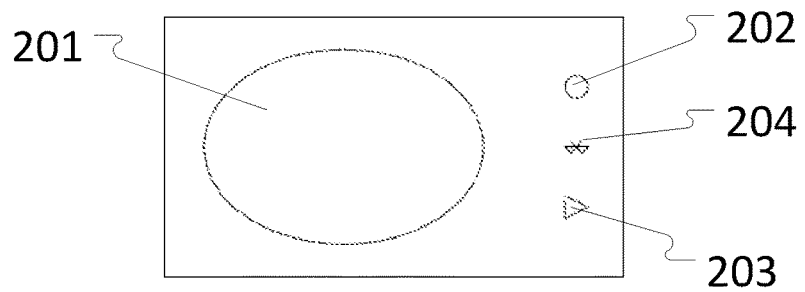

Shown in FIG. 2b is the position determination device 100 of FIG. 2a shown from 'above', i.e. shown from a direction pointing towards the activation or operation button 201 and the indicators 202, 203, and 204.

Figure 2C:
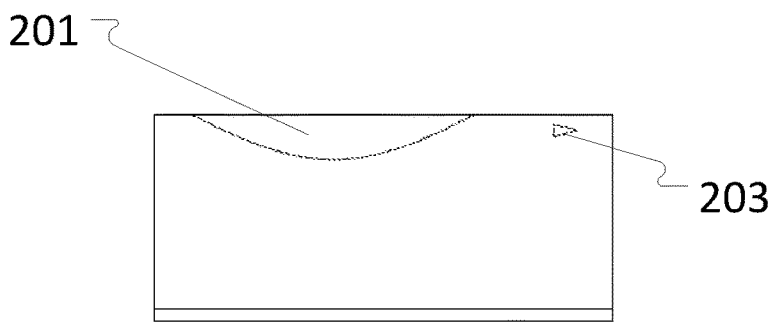

Shown in FIG. 2c is the position determination device 100 of FIG. 2a shown from one side.

Figure 2D:
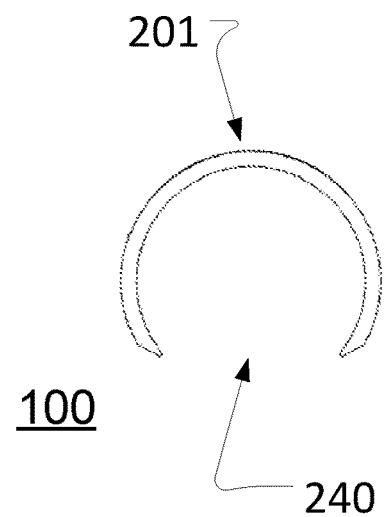

Shown in FIG. 2d is the position determination device 100 of FIG. 2a shown from one end. As can be seen, the position determination device 100 in this view has a more or less circular ring shape with an opening, recess, cut-out, or similar 240 for receiving at least a part of the liquid drug administration device when being secured to this.

The position determination device 100 may e.g. have a suitable 'soft' or flexible material on its inside on parts that are to be in contact with the liquid drug administration device when attached thereto and/or have pliable walls enabling it to 'snap' onto the liquid drug administration device 200 (and to be released therefrom again).

FIG. 3a schematically illustrates a perspective view of the position determination device of FIGS. 2a-2d being secured to a liquid drug administration device.

Shown is the position determination device 100 of FIG. 2a in a state where it is attached or secured to a liquid drug administration device 200 that e.g. may be of the type mentioned in connection with FIG. 1, and in particular a liquid insulin administration device such as an insulin pen or similar.

The liquid drug administration device 200 may be of any suitable type and in this and corresponding embodiments of the position determination device 100 it does not require any modification of the liquid drug administration device to take advantage of the present invention. Moving and using the liquid drug administration device 200 will move the position determination device 100 with a fixed positional relationship between them. If the position determination device 100 is removed and attached back onto the liquid drug administration device 200 at another position there may in certain cases be a need for re-calibration, unless the position and/or orientation of the position determination device 100 on the liquid drug administration device 200 is known a priori as disclosed herein.

FIG. 3b schematically illustrates a perspective view of the position determination device 100 and the liquid drug administration device 200 of FIG. 3a before the position determination device 100 is secured to the liquid drug administration device 200.

In this and corresponding embodiments, the position determination device 100 is simply snapped or clicked onto the liquid drug administration device 200 as indicated by the four broken lines. The shape of the position determination device 100 being generally of a hollow cylindrical shape with its opening or cut-out—as also shown in FIGS. 2a-2d—enables the position determination device 100 to easily but securely be temporarily attached or fixed to the liquid drug administration device 200.

The specific shape of the position determination device 100 of FIG. 3b and corresponding devices are particularly well suited to be secured to pen-type liquid drug administration devices. But the shape may of course vary according to the liquid drug administration device that it is to be used together with.

Alternatively, the position determination device 100 may be 'slided' onto the liquid drug administration device 200 from one of the ends. As other alternatives, the position determination device 100 may comprise one or more attachment or securing elements enabling it to be secured to the liquid drug administration device 200 in other ways (whereby the position determination device 100 may have a different shape) e.g. as described in connection with FIGS. 8 and 9.

Embodiments corresponding to the one shown in FIGS. 2 and 3 can only fit with certain designs of liquid drug administration devices 200 (although the shape and/or size may be changed). In order to accommodate a wider set of liquid drug administration devices 200 by a single position determination device 100, some embodiments of a position determination device 100 involves a main or overall body or housing that comprises or is separable into (at least) two parts with one part being an interchangeable fitter component (also referred to as a separable and interchangeable part) that is adapted to receive, attach to, or connect with a specific liquid drug administration device 200 or specific set of similar (similar in the sense that the same fitter component can receive, attach to, or connect with) type(s) of liquid drug administration devices 200 and the other part is the main part of the position determination device 100 comprising the position determination element, the one or more processing units, and other functional elements as disclosed herein.

An example of this is e.g. shown and explained in connection with FIGS. 12a and 12b. The fitter component may e.g. be simple casing produced in a wide set of variations with the purpose of locking on to the specific drug administration device (or set or class) and providing a vehicle that the main part of the position determination device 100 attaches to by one or more securing elements, e.g. a set of groves, magnets, or other suitable fixation mechanisms. In this way, only the fitter component needs to be chosen or changed to accommodate another type of liquid drug administration device.

The liquid drug administration device 200 will typically comprise at least one activation button or other activation elements to initiate the actual administration of the liquid drug to the user.

In some embodiments, the position determination device 100 will derive data (or obtain and e.g. transmit a position signal) representing an actual injection location based on the user specifically activating the liquid drug administration device 200 to administer the liquid drug.

In this way, only one activation action from the user is needed even if the position determination device 100 and the liquid drug administration device 200 are separate devices.

If the position determination device 100 is integrated with the liquid drug administration device 200 this is of course relatively easily enabled.

Even if the position determination device 100 is not integrated with the liquid drug administration device 200 an alternative measure may e.g. be that pressing the activation button or the like on the liquid drug administration device 200 physically will activate the activation button of the position determination device at the same time. It may also be the other way around where activation of the activation button of the position determination device physically will activate an activation button or the like on the liquid drug administration device 200.

This could e.g. be achieved if the position determination device 100 is located on the liquid drug administration device 200 so that the position determination device's activation button is on top of (or in any other engaging relationship with) the activation button of the drug administration device 200. It is to be understood that the specific location of the various activation buttons may be different in specific implementations.

Alternatively, a pressure sensor may e.g. be connected to the activation button of the liquid drug administration device 200 to allow the position determination device 100 to register the position at the exact moment of the injection. This pressure sensor may be manual, mechanical or may be implemented using a remote distance measurement e.g. as described in the following. This distance measurement would be used to detect movement of the activation button of the liquid drug administration device 200.

According to some embodiments, the remote distance measurement may be performed e.g. by

- using an IR light source, light sensor and a reflector having a material with predetermined reflective properties. By measuring the angle at which light from the source is reflected on the material and returned to the sensor the distance can be derived,
- by placing a magnetic source at or near the activation button and a magnetic sensor at a known, static position. In this embodiment the distance is derived by measuring the strength of the magnetic signal and comparing to a baseline for the magnetic source, and/or
- by using other distance measuring techniques such as using a camera to e.g. measure the relative size of the activation button from a static position thereby deriving the distance.

A microphone or other sound sensor may also be used as another alternative to derive data representing an actual injection location based on the user specifically activating the liquid drug administration device 200 to administer the liquid drug for those drug administration devices 200 that incorporates or produces distinct sounds for increase, decrease, and release of the drug dosage. This is common e.g. among insulin administration devices to provide user feedback and/or allow users with impaired sight to hear when the dosage is respectively increased, decreased, or released. An aspect of this and embodiments thereof are shown and explained further in connection with FIG. 10.

For liquid drug administration devices 200 that incorporate mechanical aspects to prime or set a dosage to be administered, a position determination device 100 comprising at least one accelerometer or other suitable movement detection element, the at least one accelerometer/movement detection element may according to some embodiments be used to capture the changes in dosage. An aspect of this and embodiments thereof are shown and explained further in connection with FIGS. 11, 14, 15, 16, 17, 18, and 20.

In some embodiments (including the ones explained in connection with FIGS. 1 to 2d and in the following), the position determination device 100 may further comprises an image sensor or other sensor element configured to detect an amount of liquid drug being administered by the liquid drug administration device 200. Alternatively, the amount of liquid drug being administered by the liquid drug administration device 200 may be determined as shown and described in connection with FIG. 10 and/or FIGS. 11, 14, 15, 16, 17, 18, and 20. In this way, dosage data may be collected (and communicated further on) by the position determination device 100 in situations where a liquid drug administration device 200 otherwise does not support this.

Figure 4:
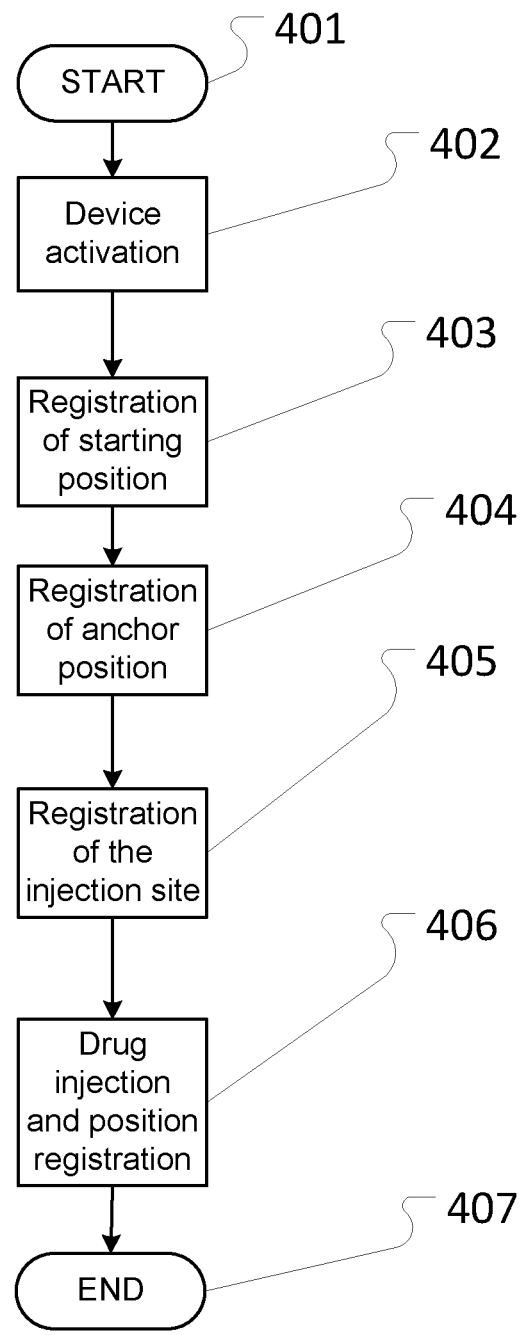
FIG. 4 schematically illustrates a flow chart of one embodiment of position determination by a position determination device e.g.

FIG. 4 schematically illustrates a flow chart of one embodiment of position determination by a position determination device e.g. as shown in FIGS. 1 to 3b, 8 to 9, 12 and embodiments thereof.

The method starts or initiates at step 401 and at step 402 the user activates the position determination device (e.g. a position determination device as disclosed herein such as one shown and explained in connection with FIGS. 1-3b, 8-9, 12, and variations thereof or alternatively of another type) by pressing an appropriate activation element (e.g. like 201 shown in FIGS. 2a-3b, and 9).

At step 403, the user moves the position determination device, or rather moves the liquid drug administration device (e.g. like 200 shown and explained in connection with FIGS. 1, 3a-3b, 8-9, 12, or alternatively of another type) with the attached or integrated position determination device to a given pre-determined or pre-selected starting position. The starting position may e.g. be the navel, a knee, an elbow, or any other appropriate starting position as calibrated and may be used as the starting point of any location determination for the associated drug injection. The starting position may e.g. be selected by the user.

After e.g. a few seconds of non-movement (or by the user activating an appropriate activation element or some other action or means), the current position (being the starting position) is automatically registered and stored as data in the memory and/or storage of the position determination device, in the memory and/or storage of a separate electric device (e.g. 300 in FIGS. 1 and 7), and/or in the memory and/or storage of a liquid drug administration device (e.g. 200 shown and explained in connection with FIGS. 1, 3a-3b, 8-9, and 12).

For relevant embodiments, at least one indicator element, e.g. a confirmation light or LED like 202 in FIGS. 2a-3b and 8-9, is activated until the position determination device 100 (and the liquid drug administration device) is moved again.

At step 404, the position determination device (and the liquid drug administration device) is moved to another location referred to as an anchor point or the like related to a desired injection location. An anchor point may e.g. be the left knee of the user if the desired injection location is at the left thigh, etc.

The anchor point location may e.g. be chosen by the user or suggested or recommended e.g. as described in connection with step 504 of FIG. 5.

After e.g. a few seconds of non-movement (or by the user activating an appropriate activation element), the current position (being the anchor point) is automatically registered and stored as data in the memory and/or storage of the position determination device, in the memory and/or storage of a separate electric device (e.g. 300 in FIGS. 1 and 7), in the memory and/or storage of a liquid drug administration device (e.g. 200 shown and explained in connection with FIGS. 1, 3a-3b, 8-9, and 12).

For relevant embodiments, the least one indicator element, e.g. the confirmation light or LED, is activated until the position determination device (and the liquid drug administration device) is moved again.

In some embodiments, the anchor point is not necessarily needed and step 403 proceeds directly to step 405. This depends on the used position determination scheme.

At step 405, the position determination device (and the liquid drug administration device) is moved to a desired injection location. The desired injection location may e.g. be chosen by the user or suggested or recommended e.g. as described in connection with step 506 of FIG. 5.

If the position of the desired injection location is determined to be too close to previous injection locations (e.g. within about 1 or about 3 cm as advised in the current state of the diabetes treatment art within a given time-frame) by the one or more processing units of the position determination device according to overall general or the user's specifically entered guidelines, then at least one indicator element, e.g. a warning light or LED like 203 in FIGS. 2a-3b and 9, will activate prompting the user that current position is not suitable or recommended for injection and that another injection location should be chosen.

The position determination device (and the liquid drug administration device) should then be moved to a new injection location and when that is done and the new injection location is determined-by the one or more processing units like described above and elsewhere-to be suitable then least one indicator element, e.g. a confirmation light or LED like 202 in FIGS. 2*a*-3*b*, is activated to signal that it is ok to perform an injection at the current injection location.

At step 406, the user activates the liquid drug administration device to administer the liquid drug at the injection location and also presses or activates an appropriate activation element (e.g. like 201 shown in FIGS. 2*a*-3*b* and 9) to register and store the position of the actual injection location as data in the memory and/or storage of the position determination device, in the memory and/or storage of a separate electric device (e.g. 300 in FIGS. 1 and 7), in the memory and/or storage of a liquid drug administration device (e.g. 200 shown and explained in connection with FIGS. 1, 3*a*-3*b*, 8-9, and 12). As noted previously, it may alternatively be the activation of the liquid drug administration device that triggers the registration and storage of the actual injection location.

Accordingly, data representing the position of the actual injection location is stored in the device itself and/or, if possible, transmitted to a separate electric device (e.g. 300 in FIGS. 1 and 7) and/or a liquid drug administration device (e.g. 200 shown and explained in connection with FIGS. 1, 3*a*-3*b*, 8-9, and 12) and stored there for later use and/or retrieval. After the transmission is completed, the position determination device may deactivate and the method ends at step 407. If transmission for some reason is not possible due to the receiving device being out of reach, being shut down, being in flight mode, or for other reasons, the device itself may deactivate as stated, and then transmit the stored data to the other device upon a subsequent activation and when possible.

Data representing a number of actual positions may in this way be collected, e.g. together with additional information, time-stamp, amount of administered liquid drug (for embodiments supporting that), etc. This provides a very comprehensive 'diary' for the user, which may be useful for a user in improving self-administration routines as well as for medical professionals e.g. to check for regimen compliance, gather data for research, improve patient education, etc.

Using both a starting point and an anchor point increases the precision of the registration of the injection location. However, in in some alternative embodiments, an anchor point may be selected in some way (e.g. by the user choosing one or by being recommending one) and the injection location is determined relative only to the selected anchor point, i.e. a starting point is not used.

Figure 5:
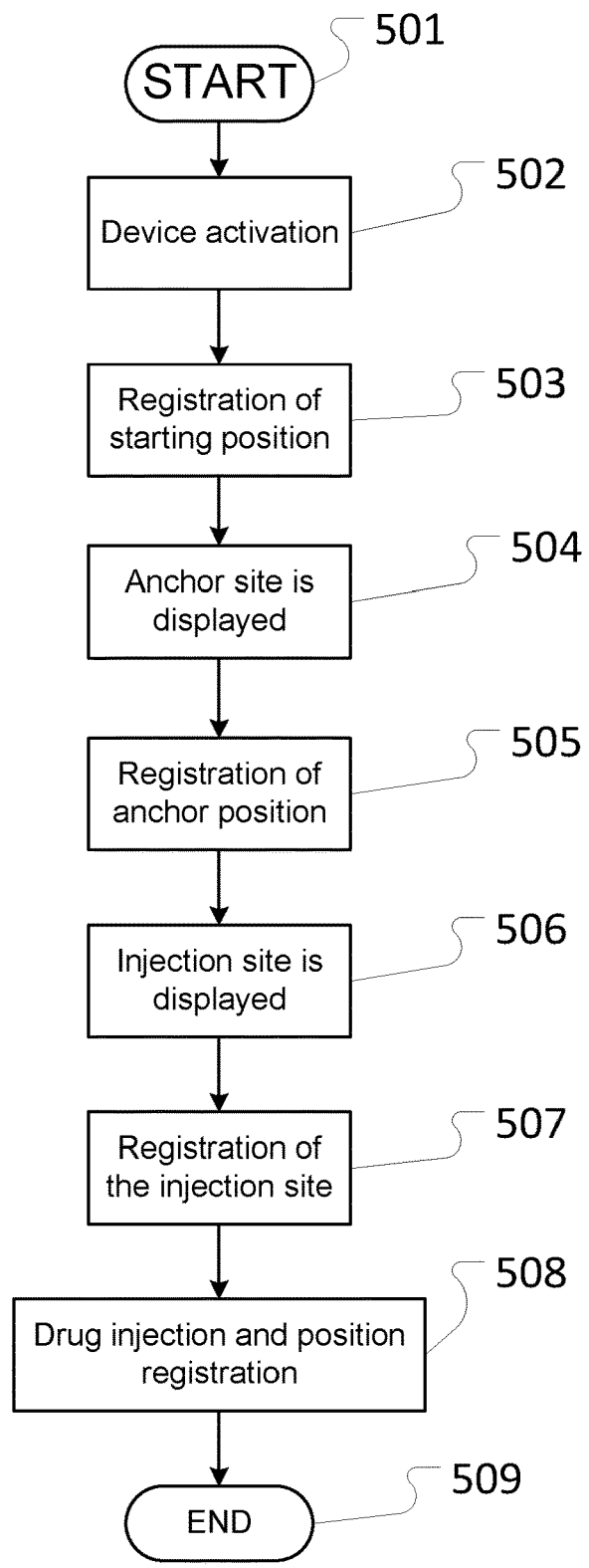
FIG. 5 schematically illustrates a flow chart of one embodiment of a method of suggesting an injection location.

FIG. 5 schematically illustrates a flow chart of one embodiment of a method of suggesting an injection location.

The method starts or initiates at step 501 and at step 502 (which may correspond to step 402 in FIG. 4) the user activates the position determination device (e.g. a position determination device as disclosed herein such as one shown and explained in connection with FIGS. 1-3*b*, 8-9, and 12, and variations thereof or alternatively of another type) by pressing an appropriate activation element (e.g. 201 shown in FIGS. 2*a*-3*b*, and 9).

At step 503 (which may correspond to step 403 in FIG. 4), the user moves the position determination device and the liquid drug administration device (e.g. like 200 shown and explained in connection with FIGS. 1, 3*a*-3*b*, 8-9, and 12, or alternatively of another type) to a given pre-determined or pre-selected starting position, e.g. like the navel, a knee, an elbow, or any other appropriate starting position as calibrated.

After e.g. a few seconds of non-movement (or by some other action or means), the current position (being the starting position) is automatically registered and stored as data in the memory and/or storage of the position determination device, in the memory and/or storage of a separate electric device (e.g. 300 in FIGS. 1 and 7), and/or in the memory and/or storage of a liquid drug administration device (e.g. 200 shown and explained in connection with FIGS. 1, 3*a*-3*b*, 8-9, and 12). For relevant embodiments, at least one indicator element, e.g. a confirmation light or LED like 202 in FIGS. 2*a*-3*b* and 9, is activated until the position determination device 100 (and the liquid drug administration device) is moved again.

At step 504, an appropriate injection location to use is derived.

Figure 7:
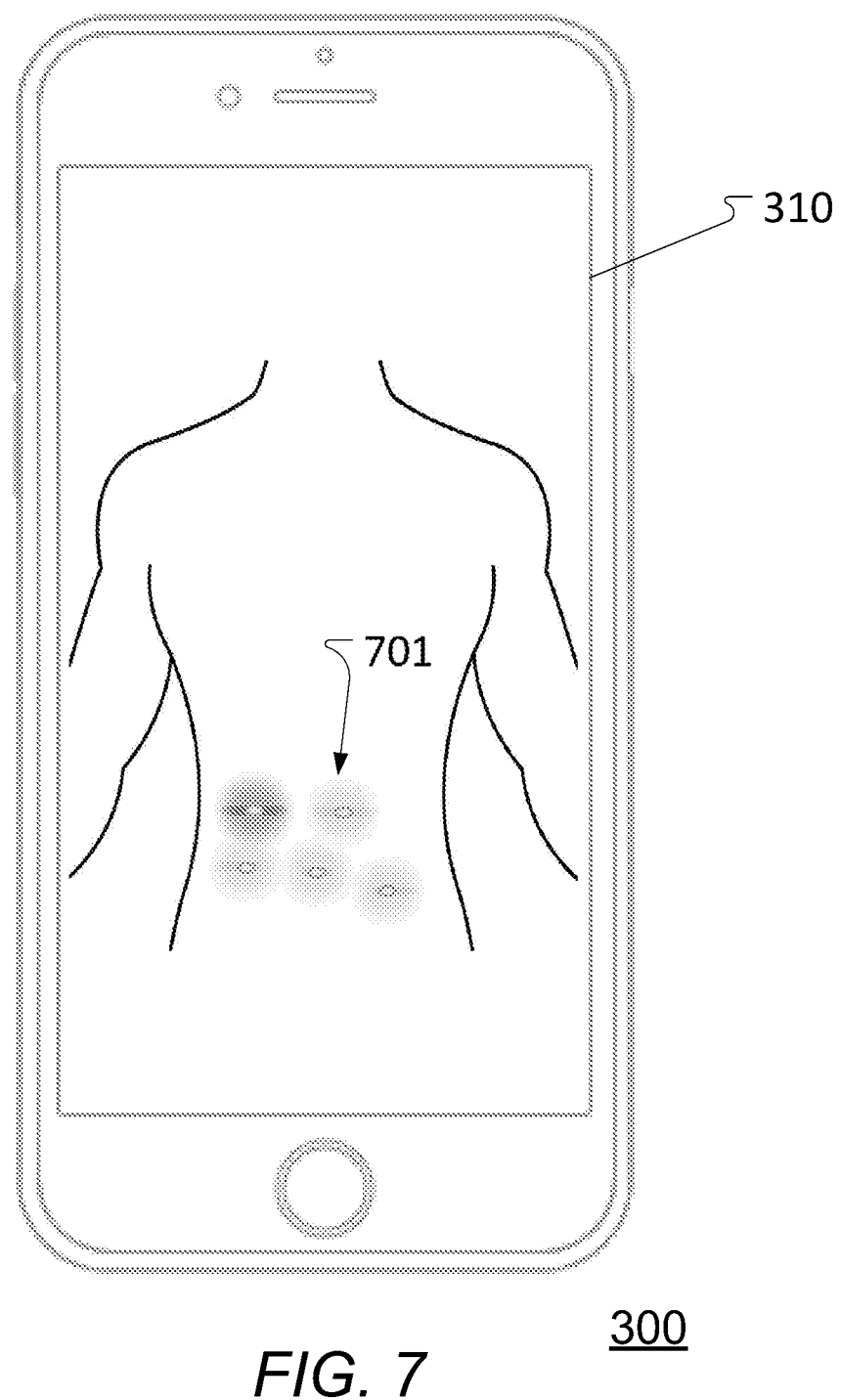
FIG. 7 schematically illustrates a separate electric device displaying a 'heatmap' view or similar of earlier injections.

The injection location to use this particular time may be derived by a separate electric device (e.g. 300 in FIGS. 1 and 7). Alternatively, it may be derived by the one or more processing units of the position determination device or a liquid drug administration unit.

The inject location to use at this time is derived according to general or the user's specifically entered guidelines stored as data. This may for example be according to a scheme where the determination of injection sites e.g. follow a circular or spiral pattern across the belly to ensure an even spread of sites over a given period like a week, a linear upward moving of sites on the thighs alternating between the right and the left, or a time-based guideline always advising about the injection site unused for the longest amount of time to ensure the largest spread. The used guidelines should be chosen based on dialogue with medical professionals and individual preferences.

After the injection location to use next has been derived, an anchor point associated with the given next injection location is presented to the user, e.g. on a display of the position determination device, the separate electric device, or in another suitable way.

At step 505, the user moves the liquid drug administration device (and thereby the position determination device) to the presented anchor point or the like of the suggest injection location. If the user moves the liquid drug administration device and the position determination device to a different location than the suggested position, a warning may e.g. displayed to the user (e.g. using at least one indicator element such as a warning light or LED like 203 in FIGS. 2*a*-3*b*, and 9) and/or on a separate electric device (e.g. 300 in FIGS. 1 and 7).

After e.g. a few seconds of non-movement (or by some other action or means), the current position (being the anchor point) is automatically registered and stored as data in the memory and/or storage of the position determination device, in the memory and/or storage of a separate electric device (e.g. 300 in FIGS. 1 and 7), and/or in the memory and/or storage of a liquid drug administration device (e.g. 200 shown and explained in connection with FIGS. 1, 3*a*-3*b*, 8-9, and 12). For relevant embodiments, the least one indicator element, e.g. the confirmation light or LED, is activated until the position determination device (and the liquid drug administration device) is moved again.

In some embodiments, the anchor point is not necessarily needed and step 503 proceeds directly to step 506. This depends on the used position determination scheme At step 506, the injection location (as being associated with the registered anchor point) to use next as derived at step 504 is displayed e.g. on the display of the position determination device, the separate electric device, or in another suitable way.

At step 507, the user moves the liquid drug administration device (and thereby the position determination device) to the presented suggested injection location.

For relevant embodiments, at least one indicator element, e.g. a warning light or LED like 203 in FIGS. 2a-3b, and 9, will activate and stay activated until the position determination device is moved within a predetermined threshold distance of the injection location that was displayed at step 506.

The predetermined threshold may be defined in the user's entered guidelines or be an overall general threshold.

For relevant embodiments, when the position determination device comes within the predetermined threshold distance of the injection location then least one indicator element, e.g. a confirmation light or LED like 202 in FIGS. 2a-3b, is activated to signal that it is ok to perform an injection at the current injection location.

At step 508, the user activates the liquid drug administration device to administer the liquid drug at the injection location and also presses or activates an appropriate activation element (e.g. like 201 shown in FIGS. 2a-3b, and 9) to register and store the position of the actual injection location as data in the memory and/or storage of the position determination device, in the memory and/or storage of a separate electric device (e.g. 300 in FIGS. 1 and 7), and/or in the memory and/or storage of a liquid drug administration device (e.g. 200 shown and explained in connection with FIGS. 1, 3a-3b, 8-9, and 12). As noted previously, it may alternatively be the activation of the liquid drug administration device that triggers the registration and storage of the actual injection location or alternatively be a dosage injection activity (e.g. determined as disclosed herein based on sound and/or vibration) that triggers the registration and storage of the actual injection location.

Accordingly, data representing the position of the actual injection location is stored in the device itself and/or, if possible, transmitted to a separate electric device (e.g. 300 in FIGS. 1 and 7) and/or a liquid drug administration device (e.g. 200 shown and explained in connection with FIGS. 1, 3a-3b, 8-9, and 12) and stored there for later use and/or retrieval. After the transmission is completed, the position determination device may deactivate and the method ends at step 509. If transmission for some reason is not possible due to the receiving device being out of reach, being shut down, being in flight mode, or for other reasons, the device itself may deactivate as stated, and then transmit the stored data to the other device upon a subsequent activation and when possible.

Figure 6:
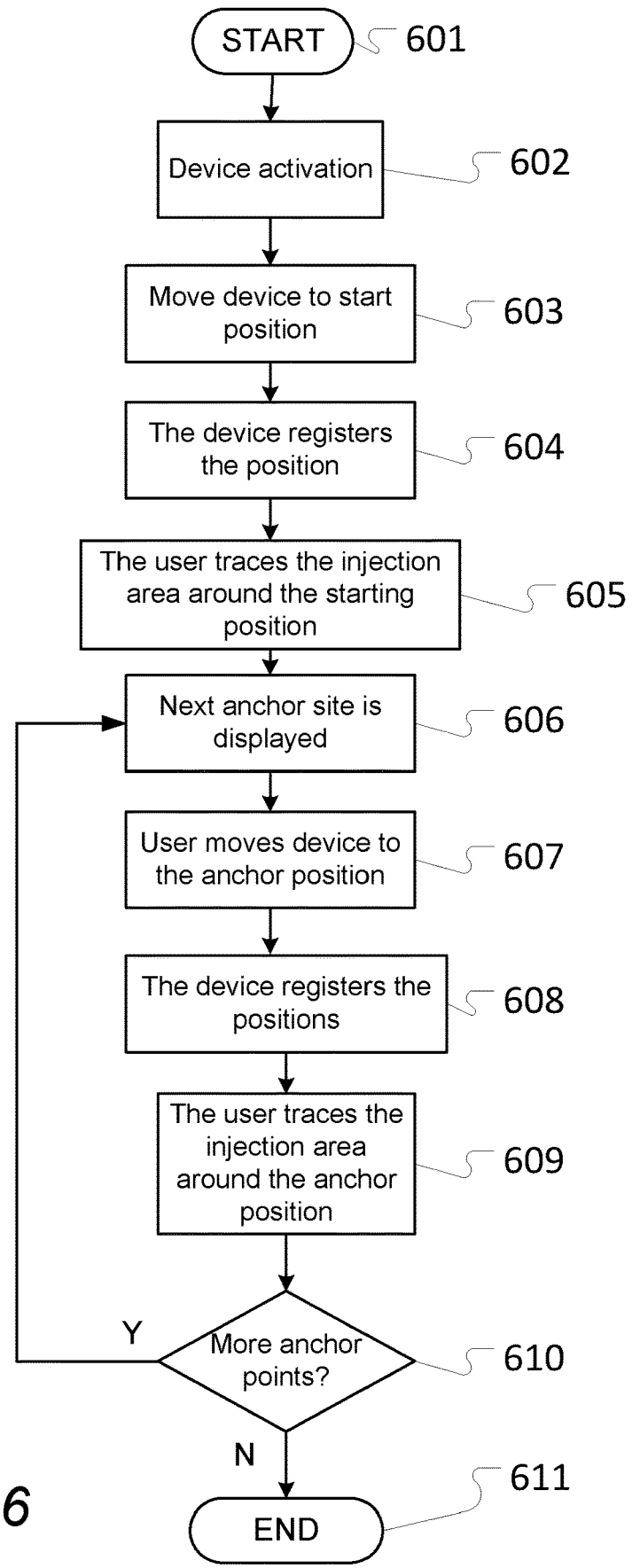
FIG. 6 schematically illustrates a flow chart of one embodiment of a calibration method of a position determination device, e.g.

FIG. 6 schematically illustrates a flow chart of one embodiment of a calibration method of a position determination device.

The method starts or initiates at step 601 and at step 602 the user activates the position determination device (e.g. a position determination device as disclosed herein such as one shown and explained in connection with FIGS. 1-3b and 8-9 and variations thereof or alternatively of another type) by pressing an appropriate activation element (e.g. 201 shown in FIGS. 2a-3b, and 9).

At step 603, the user moves the position determination device, or rather moves the liquid drug administration device (e.g. 200 shown and explained in connection with FIGS. 1, 3a-3b, 8-9, and 12) with the attached or integrated position determination device to a given pre-determined or pre-selected starting position and keeps the position determination device still. It may be that the user chooses the starting position him- or herself or that it is pre-defined and presented in some way, e.g. using a separate electric device (e.g. 300 in FIGS. 1 and 7).

This starting position is intended to be used for the following position determinations (e.g. at least until a next (re-)calibration).

At step 604, the user activates an appropriate activation element and the current position (being the starting position) is then registered and stored as data in the memory and/or storage of the position determination device, in the memory and/or storage of a separate electric device (e.g. 300 in FIGS. 1 and 7), and/or in the memory and/or storage of a liquid drug administration device (e.g. 200 shown and explained in connection with FIGS. 1, 3a-3b, 8-9, and 12).

At step, 605 the user indicates a boundary of the injection area that is to be associated with the starting position (if there is one to be associated). In some embodiments, this may be done by the user moving the position determination device from the starting position to an edge of the injection area and then, while keeping the activation element active or pressed, the user traces the edge of the injection area with the position determination device (being attached or integrated with the liquid drug administration device). Alternatively, other ways to indicate the boundary and/or the injection area may be used.

The position determination device then registers and stores the injection area and/or boundary as data in its memory and/or storage and/or transmits the data to the separate electric device (e.g. 300 in FIGS. 1 and 7) and/or a liquid drug administration device (e.g. 200 shown and explained in connection with FIGS. 1, 3a-3b, 8-9, and 12a-12b) for storage and/or visual feedback to the user.

At step 606, the separate electric device displays or presents information to the user about which anchor position to register. Alternatively, the position determination device or a liquid drug administration unit displays or presents the information to the user.

At step 607, the user moves the position determination device and the liquid drug administration device to the shown anchor position.

At step 608, the current position (being the anchor point) is automatically registered and stored as data in the memory and/or storage of the position determination device, in the memory and/or storage of a separate electric device (e.g. 300 in FIGS. 1 and 7), and/or in the memory and/or storage of a liquid drug administration device (e.g. 200 shown and explained in connection with FIGS. 1, 3a-3b, and 8-9) e.g. by keeping the position determination device still for a predetermined amount or time or by activating an appropriate activation element (e.g. 201 shown in FIGS. 2a-3b, and 9). For relevant embodiments, the least one indicator element, e.g. the confirmation light or LED, is activated after registration until the position determination device (and the liquid drug administration device) is moved again.

At step 609, the user indicates the boundary of the injection area that is to be associated with the current anchor position and it is registered and stored in the same manner as at step 605 for the starting position.

At step 610 it is checked whether this procedure is to be done for any further anchor points. If yes, the method loops back to step 606 whereby steps 606-610 is repeated in connection with the next anchor point. If no (signifying no remaining anchor points), the calibration process terminates at step 611.

In this way, simple and reliable calibration is provided.

It is noted, that the methods illustrated and described in connection with FIGS. 4, 5, and 6 and embodiments and variations thereof each (individually or in any combination) may be used independently of the described aspects and embodiments of the position determination device as disclosed herein although they together work especially well.

FIG. 7 schematically illustrates a separate electric device displaying a 'heatmap' view or similar of earlier injections.

Shown is a separate electric device 300, e.g. corresponding to the one shown in FIGS. 1 and 7, having a display 310 to be used according to some aspects in connection with some embodiments of a position determination device as disclosed herein (e.g. such as 100 shown in FIGS. 1-3b, 8-9, and variations thereof or of another type) and a liquid drug administration device (e.g. such as 200 shown in FIGS. 1 and 3a-3b, 8-9, and 12, and variations thereof, or of another type).

As already mentioned, actual injections locations may preferably be registered on an ongoing basis using the position determination device and the liquid drug administration device.

According to these aspects, the actual injection locations may be shown as a graphical representation of data generally known as a 'heat map' or similar where the individual values (location e.g. together with further relevant information like time of injection, actual amount of injected liquid drug, etc.) are represented as colors in a color scheme superimposed on a picture or a graphic representation of the overall injection area(s), e.g. like the torso, the thighs, upper arms, or what other injection area the user has defined, etc. The values may e.g. be stored in a matrix data structure and/or any other suitable data structure.

The color scheme may e.g. be one from green to red where a given injection location is marked yellow if it was taken in (too) close proximity (e.g. within 1 or 3 cm, or as chosen by the user) to one another injection location made within a predetermined time (e.g. a week or other timeframe as e.g. determined by the user), and red if it is in (too) close proximity to 2 or more injection locations, and green in all other cases.

The heatmap may be updated from the device when activated thus enabling the user to check an intended injection location in relation to previous injection locations.

In a recommendation mode (e.g. as indicated in FIG. 5), the device itself may show status of injection locations based on the same color scheme or recommend locations based on the chosen rotation principles and e.g. assessment of possible lipohypertrophy by medical professionals thereby guiding the user to a suitable injection site. In some further embodiments, this involves showing injection history, areas to avoid because of lipohypertrophy, and/or areas to inject in.

The aspect(s) of showing previous injection locations like this may be used independently of the described aspects and embodiments of the position determination device as disclosed herein although they together work especially well.

FIG. 8 schematically illustrates an embodiment of a locking mechanism for attaching an embodiment of a position determination device to a drug administration device.

Shown is an embodiment of a position determination device 100 as disclosed herein being attached to a drug administration device, here in the form of an insulin pen or other pen type liquid drug administration device, as well as an enlargement illustrating further details.

In this and corresponding embodiments, the position determination device 100 as disclosed herein comprises one exemplary embodiment of an attachment element in the form of a locking mechanism 701 configured to releasably engage with a mating or corresponding locking mechanism 801 of the liquid drug administration device 200. The shown drug administration device 200 comprises a cap 210 and a main body 211. More specifically, the locking mechanism 701 is configured to engage with a locking mechanism 801 of the main body 211 of the drug administration device 200 that normally is used to engage a locking mechanism of the cap 210, i.e. the locking mechanism 701 of the position determination device 100 corresponds to the locking mechanism of the cap in that they will be the same or at least similar or compatible.

In some further embodiments, and as shown, the locking mechanism 701 is further configured to engage with the locking mechanism 702 of the cap 210 (see e.g. also 702 in FIG. 9) so that the cap 210 still can be attached to the drug administration device 200 even with the position determination device 100 in place, now just connecting with the position determination device 100 instead of directly to the drug administration device 200.

The locking mechanism 701 allows the user an easy way to attach/detach the position determination device 100 to/from the drug administration device 200 in a reliable way. The specific embodiment of such a locking mechanism 701 will typically depend on the specific shape, size, and/or form of the cap 210 of the drug administration device 200 and how this attaches to the main body of the drug administration device 200.

Figure 9A:
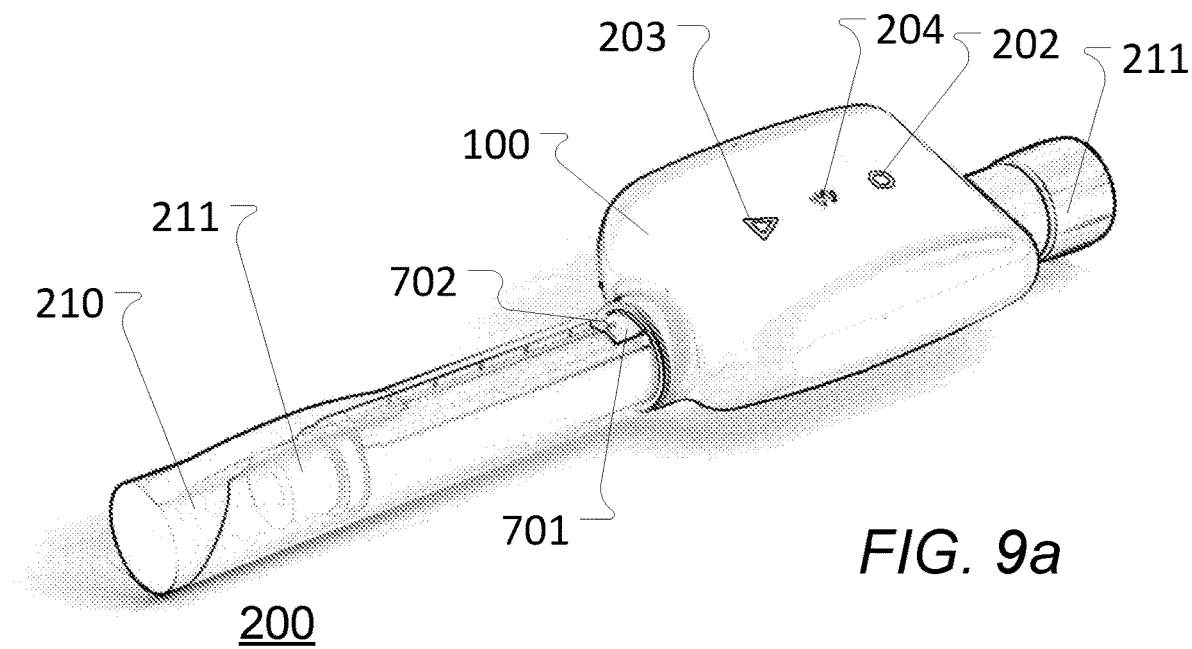
FIGS. 9a and 9b schematically illustrate an embodiment of a position determination device as disclosed herein attached to a drug administration device and by itself.
Figure 9B:
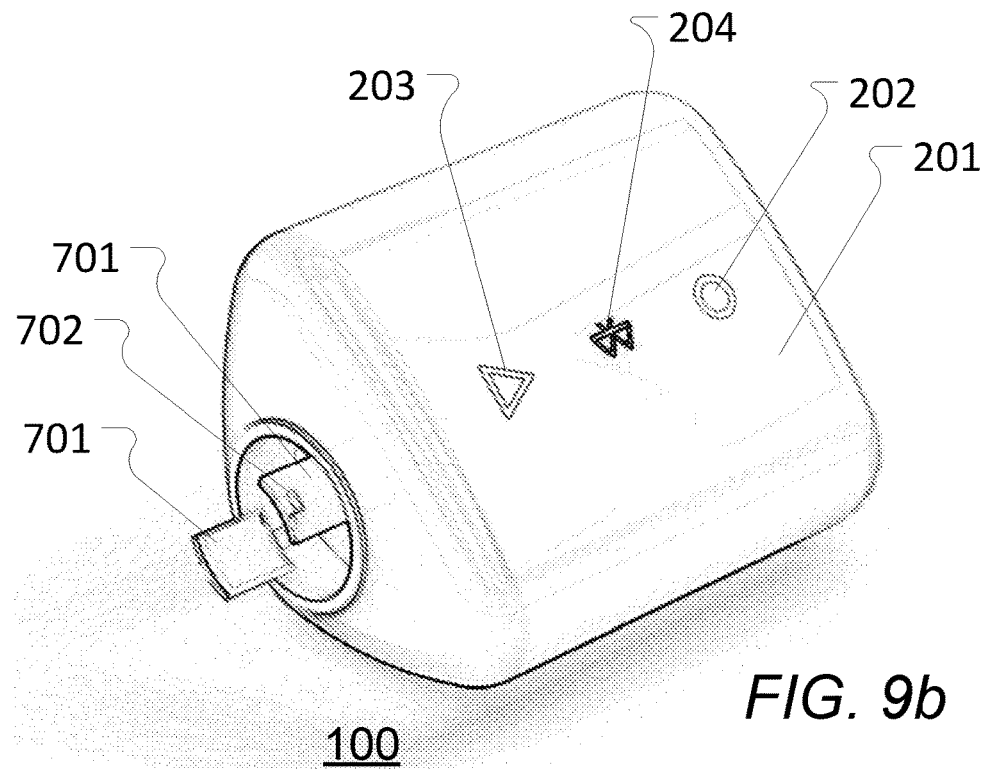

FIGS. 9a and 9b schematically illustrate an embodiment of a position determination device as disclosed herein attached to a drug administration device and by itself.

Shown in FIG. 9a is illustrated an embodiment of a position determination device 100 attached to a drug administration device 200 as disclosed herein, respectively, where the cap 210 of the drug administration device 200 is also attached to the main body 211 of the drug administration device 200. The cap 210 is shown transparently and with a cut-out to illustrate parts of the main body 211 of the drug administration device 200. The attachment is done using a locking mechanism 701 as disclosed herein. In some embodiments of the locking mechanism 701, and as shown, it further comprises an engaging element 702 for allowing a locking mechanism of the cap 210 to engage so that the cap 210 may be attached to the position determination device 100 instead of to the main body 211 of the liquid drug administration device 200 (see e.g. also FIG. 8).

The shown liquid drug administration device 200 also comprises an activation button 201, as well as a number of indicator elements here in the form of a confirmation light or LED 202, a warning light or LED 203, and a wireless communications connection light or LED 204 for user feedback as disclosed herein.

Figure 10:
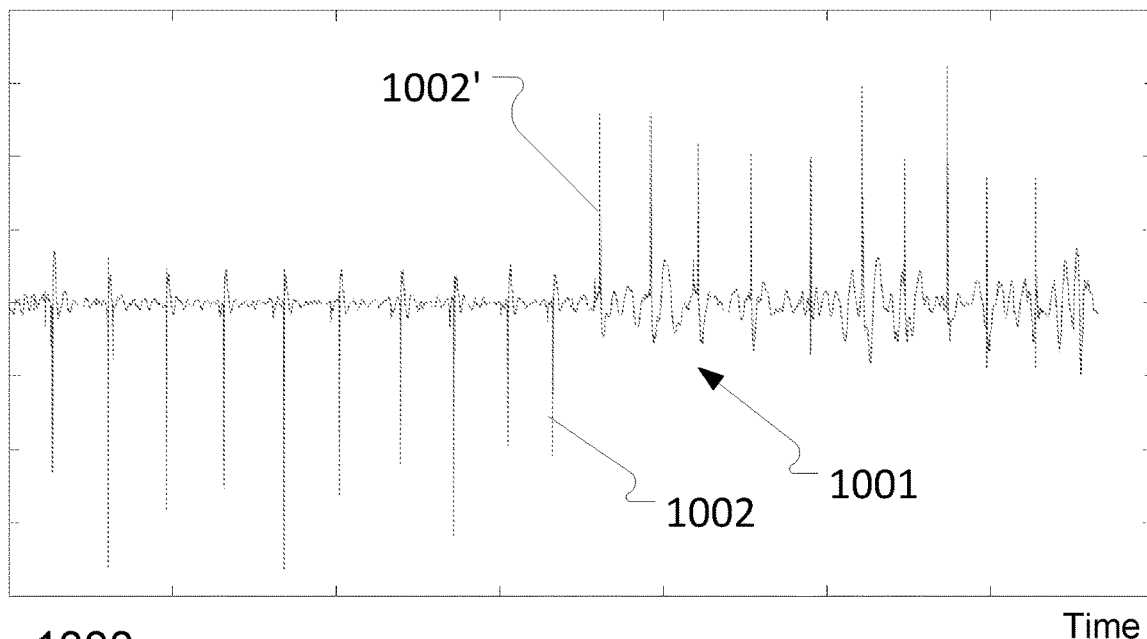
FIG. 10 schematically illustrates an exemplary sound signal emitted from a liquid drug administration device when incrementing and decrementing 10 drug dosage units, respectively.

FIG. 10 schematically illustrates an exemplary sound signal emitted from a liquid drug administration device when respectively incrementing and decrementing 10 (as an example) drug dosage units.

The liquid drug administration device may e.g. be one as disclosed herein or alternatively of another type as long as it generates distinct sounds in connection with dosage increments and decrements. As mentioned, such distinct sounds are common among insulin administration devices and some other types of drug administration devices to provide user feedback and/or allow users with impaired sight to hear when the dosage is respectively increased or decreased. Many devices also generate a different sound in connection with release or administration of the drug. The sounds need not necessarily be distinct by design. It will suffice as long as the sounds are distinct enough for the used detection scheme.

Shown is a graph 1000 comprising an exemplary sound signal or profile 1001 (forth only denoted sound profile) as obtained by a suitable sound sensor where the x axis indicates time and the y axis indicates amplitude of the sound profile 1001.

The graph illustrates as an example a sound signal or profile of the distinct "click-sounds" as emitted by a liquid drug injection device for 10 dosage increments followed by 10 dosage decrements.

The graph clearly shows 20 distinct spikes and each dosage increment and each dosage decrement clearly produces a respective distinct spike 1002, 1002' in the obtained sound profile. The dosage increments spikes 1002 are similar to each other and the dosage decrement spikes 1002' are similar to each other. Furthermore, the dosage increments spikes 1002 are quite different to the dosage decrement spikes 1002'. This enables the spikes to be differentiated from each other (and from noise) and enables identification or classification of what type of dosage action (increment or decrement) was taken by the user. A dosage increment or decrements is typically associated with a predetermined change in dose/units of the drug.

In this way, it is possible to exactly and reliably derive the amount of drug that is administered by 'counting' the pulses of each type (by obtaining the sound profile by a sound sensor and analyzing the sound profile to identify the respective spikes and their type).

For sound profiles of the type shown in FIG. 10, a determination of whether a spike is related to a dosage increment or a dosage decrement may simply (but still reliably) e.g. be done by locating amplitude values respectively above/below a predetermined max/min threshold (e.g. being dependent on the specific liquid drug administration device), by determining on what side (above/below) of an amplitude baseline a particular spike is, or by any other suitable method. Spikes above or below a certain threshold from the baseline could be filtered out or ignored.

As mentioned, a further distinct sound (and thereby further distinct spike) may also be generated by drug release thereby enabling corresponding determination of exactly when the drug is released by analyzing the sound profile in a corresponding way as disclosed herein or in another suitable way.

Additionally, determined distance between spikes, determined number of spikes, determined shape of the sound signal or parts thereof, etc. may e.g. be compared with anticipated/predetermined distance between spikes, anticipated/predetermined number of spikes, anticipated/predetermined shape of signal or parts thereof, etc. when determining whether a spike is related to a dosage increment, decrement, and/or release/administration.

As an example, a sound profile may e.g. be captured by an appropriate sound sensor and 'translated' into changes in (increment or decrement) and/or release/administration of dosage e.g. using digital or analogue signal processing techniques, e.g. as disclosed herein.

In some embodiments, two or more separate sound sensors is used to filter out background noise and enhance the signal available for processing as generally known, e.g. also using information relating to distances between the separate sound sensors.

The sound sensor(s) may e.g. be comprised by a position determination device (e.g. as disclosed herein or alternatively of another type), by a separate electric device (e.g. as disclosed herein or alternatively of another type), and/or a liquid drug administration device (e.g. as disclosed herein or alternatively of another type).

This particular aspect is generally independent of the described aspects and embodiments of the position determination device as disclosed herein (and other disclosed aspects) although they together work especially well. If this aspect is combined with the aspect of location determination as disclosed herein, identification of actual release/administration may be used as a trigger for obtaining an identified location of the liquid drug administration device to be an actual injection location.

Figure 11:
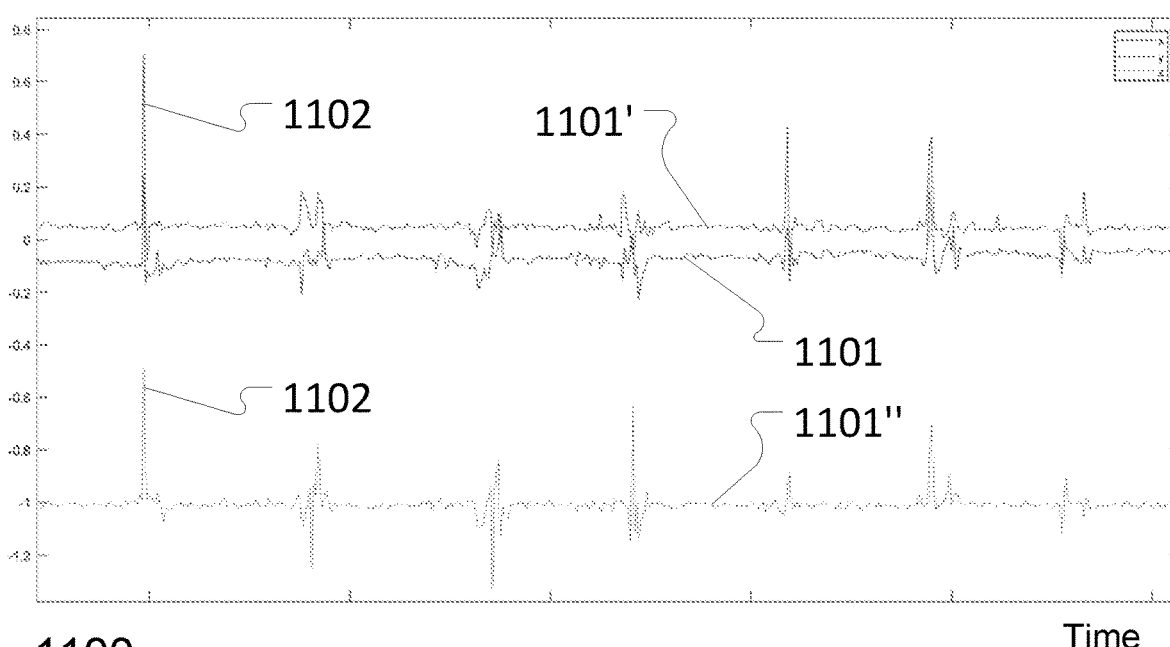
FIG. 11 schematically illustrates an example of vibrations emitted by a liquid drug administration device, as measured by an accelerometer or similar, when increasing the drug dosage by 7 units.

FIG. 11 schematically illustrates an example of vibrations emitted by a liquid drug administration device, as measured by an accelerometer or similar, when increasing the drug dosage by 7 (as an example) units.

The liquid drug administration device may e.g. be one as disclosed herein or alternatively of another type as long as it incorporate mechanical aspects to prime and/or set (increment and/or decrement) a dosage to be administered.

The accelerometer or similar may e.g. be comprised by the liquid drug administration device or alternatively it could be comprised by a position determination device as disclosed herein or another device in vibratory transferring contact (at least during use) with the liquid drug administration device.

Shown is a graph 1100 comprising three exemplary vibration signals 1101, 1101', 1101" as obtained by at least one (3D or three-axis) accelerometer or other suitable movement detection element where the x axis indicates time and the y axis indicates extent of acceleration force of the vibration signals 1100, 1100', 1100". Each of the three vibrations signals is associated with a different axis (1100: x,1100': y, 1100": z) of the accelerometer or movement detection element.

These particular exemplary vibration signals 1101, 1101', 1101" have been obtained for a drug administration device that incorporates a spring mechanism for priming the dosage.

As clearly can be seen, seven spikes 1102 are present in each vibration signal 1101, 1101', 1101"—one for each of the exemplary seven drug dosage unit increases.

Each dose increase is associated with a signal (spike) along all three axes (thereby being present in all the three vibration signals although potentially to a different extent). The strength or extent and profile of the signal may be different for other types of drug administration devices.

The vibration signals, once obtained, may 'translated' into changes in dosage using e.g. digital or analogue signal processing techniques as disclosed herein or other, e.g. somewhat along the lines as explained in connection with FIG. 10 or any other suitable 'spike detection' method. Predetermined vibration profiles (e.g. for several different liquid drug administration devices) may also be stored and compared to the obtained vibration signals to derive the information.

In this way, at least one accelerometer or movement detection element may be used to reliably capture the changes in dosage using vibration signals. As further disclosed herein the vibration signals may also be gyrometer signals or other suitable signals.

Having at least three vibrations signals readily available to analyze and derive information from (where a spike is present at least to some extent in all the three at least sometimes; in some situations a spike may only be (significantly) present in one or two of the vibration signals) increases the reliability and thereby accuracy of registering setting of a specific dosage (increment and/or decrement) to be administered by the liquid drug administration device using vibration signals. As disclosed herein, some of the at least three vibration signals (even with relatively smaller extent) may be used to reduce noise or detect otherwise false positives for the other of the at least three vibration signals and/or the at least three vibration signals may be combined into fewer or even a single combined signal being more robust in relation to noise.

Similarly, vibration signals may likewise be used for detecting decreasing a drug dosage and/or actual drug administration, i.e. actual release of a set amount of a liquid drug.

In some embodiments, a plurality of accelerometers and/or a plurality of gyrometers, or other movement detection elements may be used to measure the vibrations of the drug administration device which can be used to further reduce any (background) noise.

To further increase precision and reliability of detecting dosage settings (and dosage delivery), a combination of both sound signals (e.g. as described in connection with FIG. 10) and acceleration/gyrometer signals or other movement detection sensor signals (e.g. as described in connection with FIGS. 11 and 15-19) may be used. In such embodiments, each sensor setup, could measures the drug dosage independently and may subsequently be combined into a single measurement for drug dosage.

This particular aspect is generally independent of the described aspects and embodiments of the position determination device as disclosed herein (and other disclosed aspects) although they together work especially well.

Figure 12A:
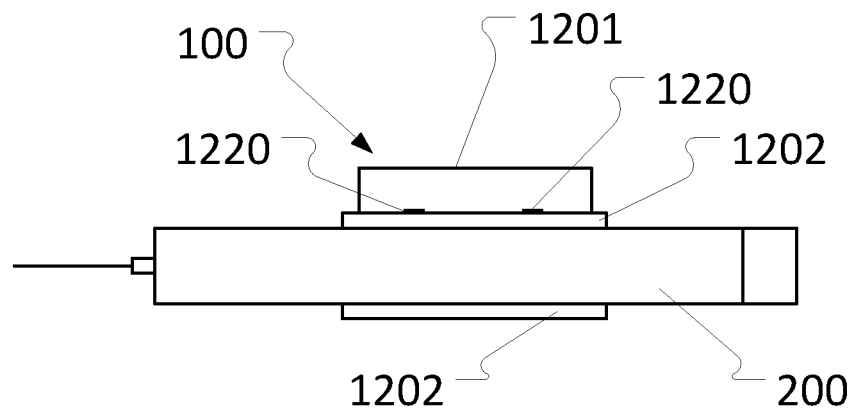
FIGS. 12a and 12b schematically illustrate an embodiment of a position determination device comprising a main or overall body or housing that is separable into two parts with one part being an interchangeable fitter component that is adapted to receive or attach to a specific liquid drug administration device.
Figure 12B:
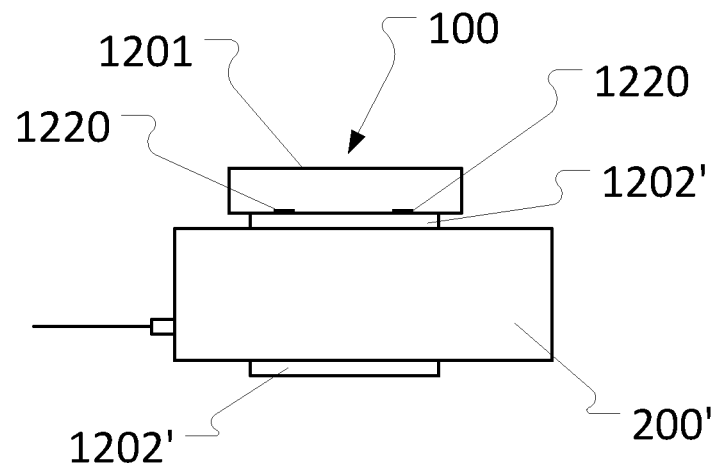

FIGS. 12a and 12b schematically illustrate an embodiment of a position determination device comprising a main or overall body or housing that is separable into two parts with one part being an interchangeable fitter component that is adapted to receive or attach to a specific liquid drug administration device.

Illustrated in FIG. 12a is cross section of a position determination device 100 and a liquid drug administration device 200 as generally disclosed herein. The liquid drug administration device 200 is a liquid drug administration device 200 of a first type, i.e. a first liquid drug administration device 200. The position determination device 100 comprises a main body or housing 1201 and a first separable and interchangeable part 1202 (also referred to herein as fitter or fitter component) being attached, in this particular and corresponding embodiments, to the main body or housing 1201 via a number (here two as an example) of securing elements 1220. The first separable and interchangeable part 1202 also connects with (or otherwise accommodates) the first liquid drug administration device 200, in this particular example by receiving it (fully or partly). The main body or housing 1201 comprises the position determination element, the one or more processing units, and other functional elements as disclosed herein.

Illustrated in FIG. 12b is a cross section of a position determination device 100 with the same main body or housing 1201 as in FIG. 12a but now attached to a different separable and interchangeable part 1202' (i.e. a second separable and interchangeable part 1202') that connects with (or otherwise accommodates) a second liquid drug administration device 200' being of different shape, type, etc. than the first liquid drug administration device 200.

As can be seen, this allows for changing between respective separable and interchangeable parts only in order to accommodate or connect the position determination device 100-or rather its main body or housing 1201-with different drug administration devices.

In some alternative embodiments, the main body or housing 1201 and the respective separable and interchangeable part 1202, 1202', when joined or attached together, are configured to receive and/or accommodate a respective liquid drug administration device 200, 200'.

This particular aspect is generally independent of the described aspects and embodiments of the position determination device as disclosed herein (and other disclosed aspects) although they together work especially well.

Figure 13:
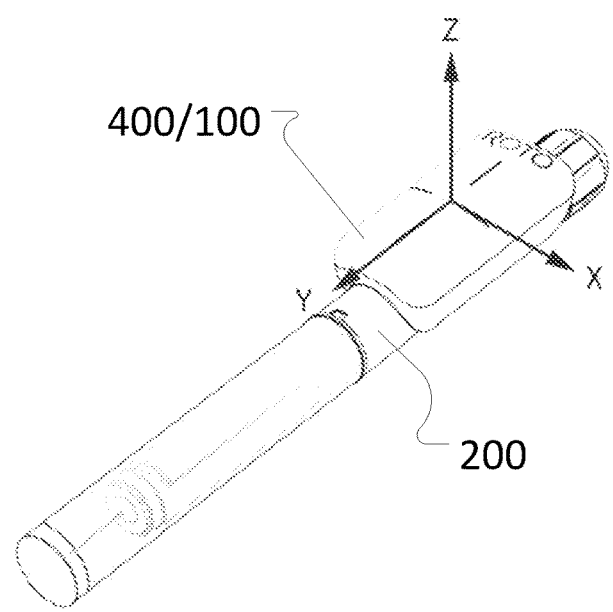
FIG. 13 schematically illustrates an exemplary dosage determination device as disclosed herein and a liquid drug administration device illustrated together with an imposed coordinate system of axes for a vibration determination element of the dosage determination device.

FIG. 13 schematically illustrates an exemplary dosage determination device as disclosed herein and a liquid drug administration device illustrated together with an imposed coordinate system of axes for a vibration determination element (comprising one or more vibration sensors) of the dosage determination device.

Shown is an exemplary dosage determination device 400 and liquid drug administration device 200 shown together with an imposed coordinate system of orthogonal axes (x, y, z) for a vibration determination element of the dosage determination device 400. In this particular example, the y axis coincides and is parallel with the length of the liquid drug administration device 200 being a pen-type liquid drug administration device. The exemplary coordinate system is a reference coordinate system for the vibration determination element comprising one or more vibration sensor(s) used for the exemplary signals shown in FIGS. 14-19.

In some embodiments, the dosage determination device 400 is (also) a position determination device 100 as disclosed herein although it does not need to be. In such embodiments, the vibration determination element may be the position determination element (denoted 110 elsewhere) as disclosed herein.

In some embodiments (and as shown), the dosage determination device 400 is (e.g. releasably) attachable to a liquid drug administration device 200 as disclosed herein—even if not implementing location determination. In other embodiments, the dosage determination device 400 (or at least its functionality) is integrated or implemented in a liquid drug administration device 200 e.g. as disclosed herein.

Figure 14:
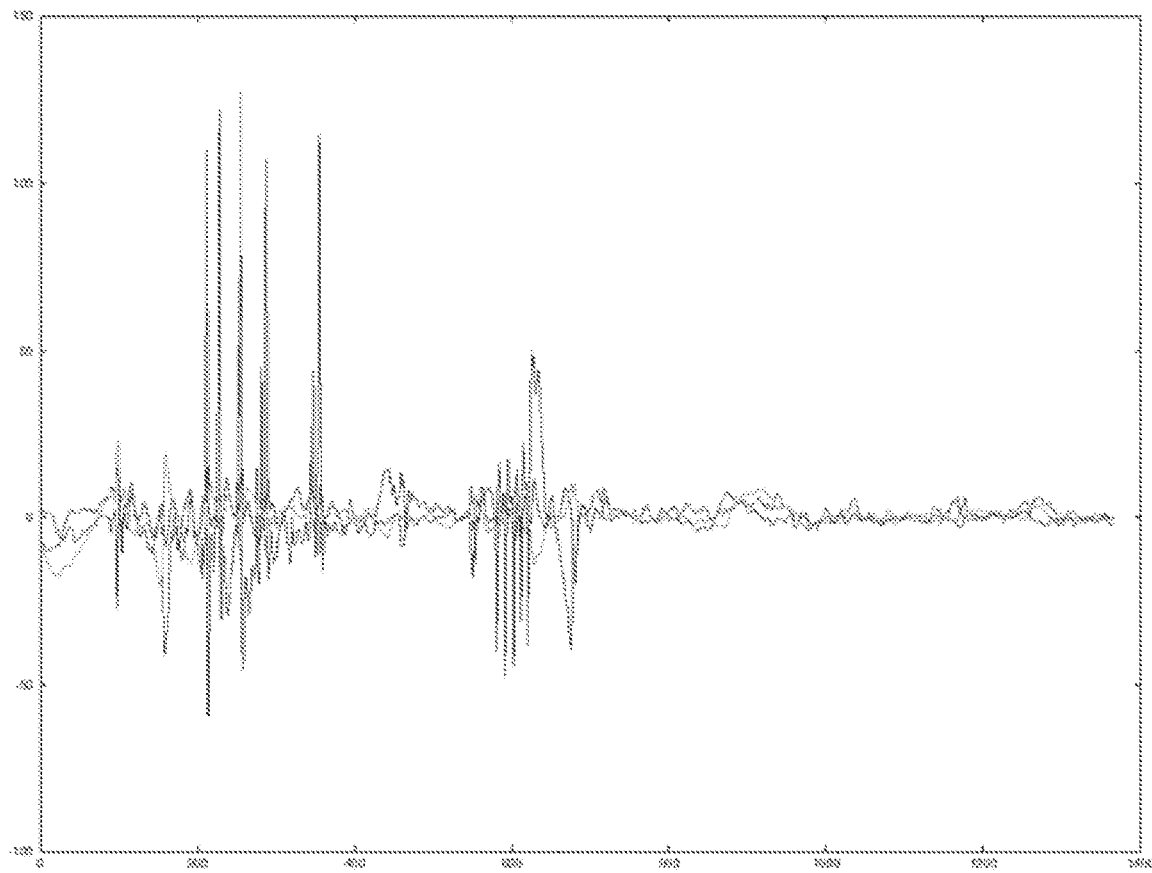
FIG. 14 schematically illustrates three exemplary gyrometer signals obtained according to the reference coordinate system of axes of FIG. 13 by a vibration determination element comprising a (three-axes) gyrometer or similar, when increasing the drug dosage by 5 units followed by decreasing the drug dosage by 5 units for a liquid drug administration device.

FIG. 14 schematically illustrates three exemplary gyrometer signals obtained according to the reference coordinate system of axes of FIG. 13 by a vibration determination element comprising a (three-axes) gyrometer or similar, when increasing the drug dosage by 5 units followed by decreasing the drug dosage by 5 units for a particular liquid drug administration device.

As can be seen, it is not straight forward to analyse such raw or unprocessed gyrometer vibration signals for the presence of any signals indicative of activities (increment and/or decrement and/or actual dosage injection). Furthermore, the vibration signals may also comprise noise e.g. due to sensor noise and/or movement of the dosage determination device 400 and/or the liquid drug administration device 200 by the user during operation.

It would be beneficial, to provide reliable and robust dosage detection or classification of signals indicative of dosage activities (increment and/or decrement and/or dosage injection). In particular it would be beneficial to provide such that minimize false positives and/or maximize true positives and in particular maximizes precision (defined as a rate of true positives compared to all detected dosage activities-both true and false) and/or recall (defined as a rate of true positives compared to all dosage activities that actually occurred). A dosage determination device 400 providing this is disclosed herein and e.g. explained further in connection with FIGS. 15-20.

The illustrated signal values are obtained by one specific type of dosage determination device 400 comprising a specific make of vibration sensor and being attached to one specific liquid drug administration device 200. The vibration signals will differ according to types of these. However, the dosage detection or classification processing as disclosed herein is general in the sense that it can be calibrated or fitted for other types of dosage determination devices, vibration sensors, and/or liquid drug administration devices.

Figure 15A:
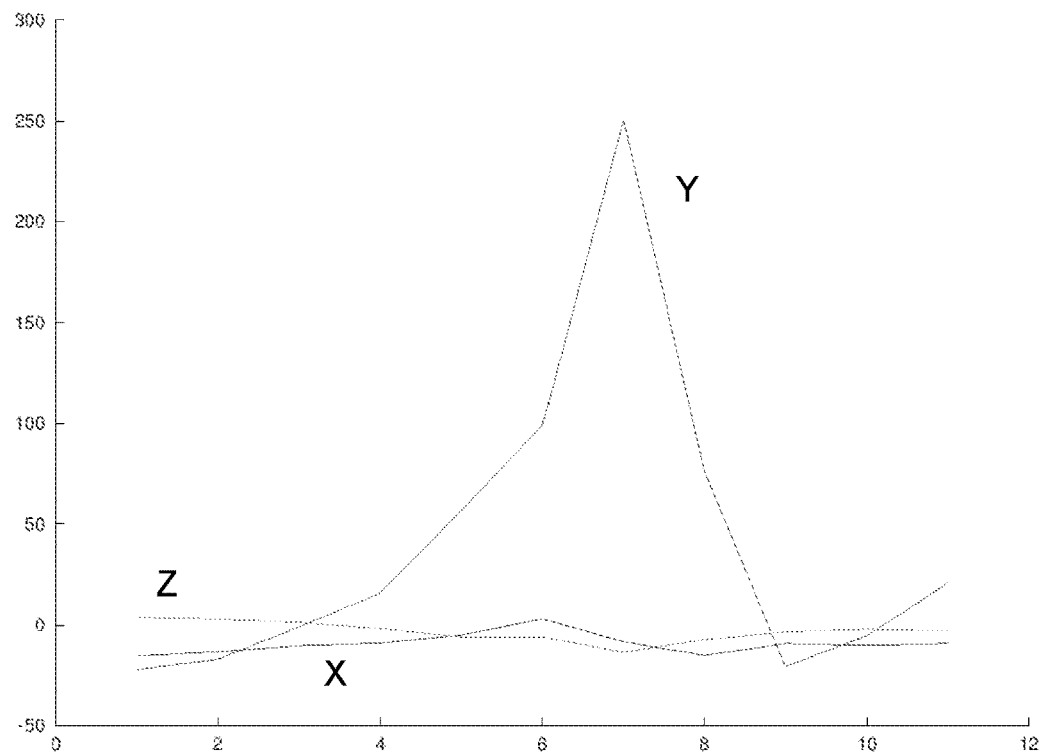
FIG. 15a schematically illustrates exemplary vibrations emitted by a liquid drug administration device, as measured by a gyrometer or similar, for a single dosage increment of a first type.

FIG. 15a schematically illustrates exemplary vibrations emitted by a liquid drug administration device, as measured by a (three-axes) gyrometer or similar, for a single dosage increment of a first type.

FIG. 15a illustrates three raw or unprocessed gyrometer signals as measured by a (three-axes) gyrometer or similar according to the exemplary reference coordinate system of FIG. 13 for a particular type of dosage determination device (and used vibration sensor) and particular type of liquid drug administration device.

One of the gyrometer signals (the signal obtained according to the y axis) is characterised by a relatively sharp rise followed by a relatively sharp fall.

Figure 15B:
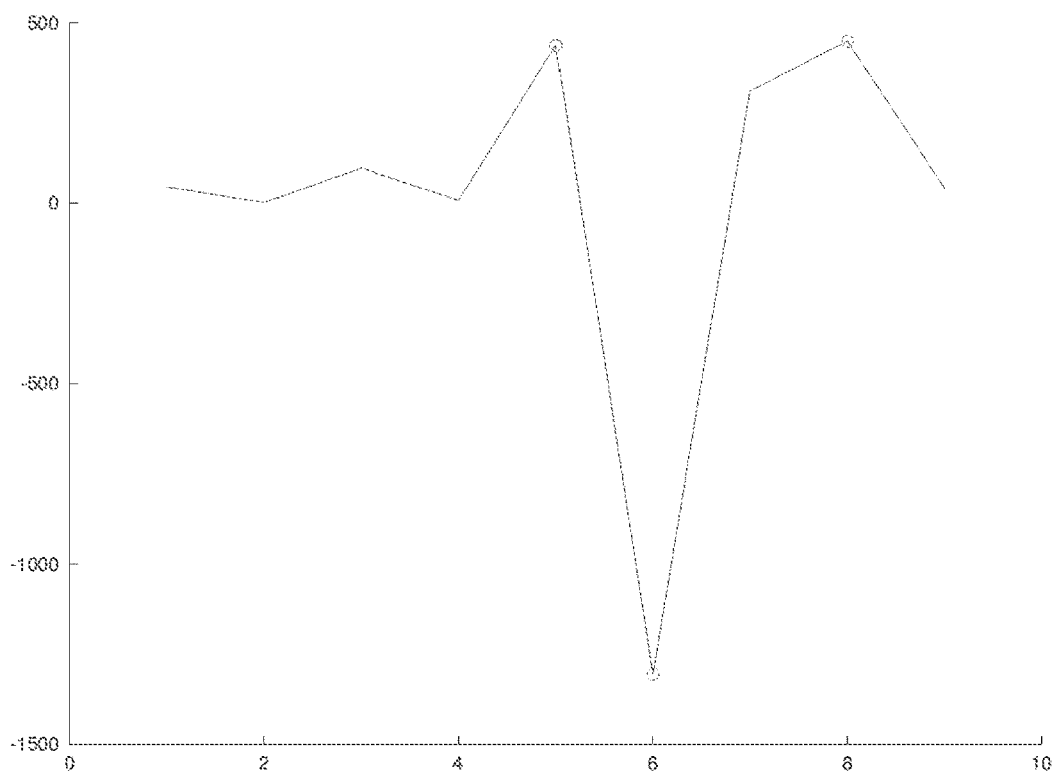
FIG. 15b schematically illustrates an exemplary dosage classification signal obtained by processing at least some of the signals of FIG. 15a according to a dosage classification or identification aspect of the present invention as disclosed herein and with one embodiment thereof being illustrated in FIG. 20.
Figure 20:
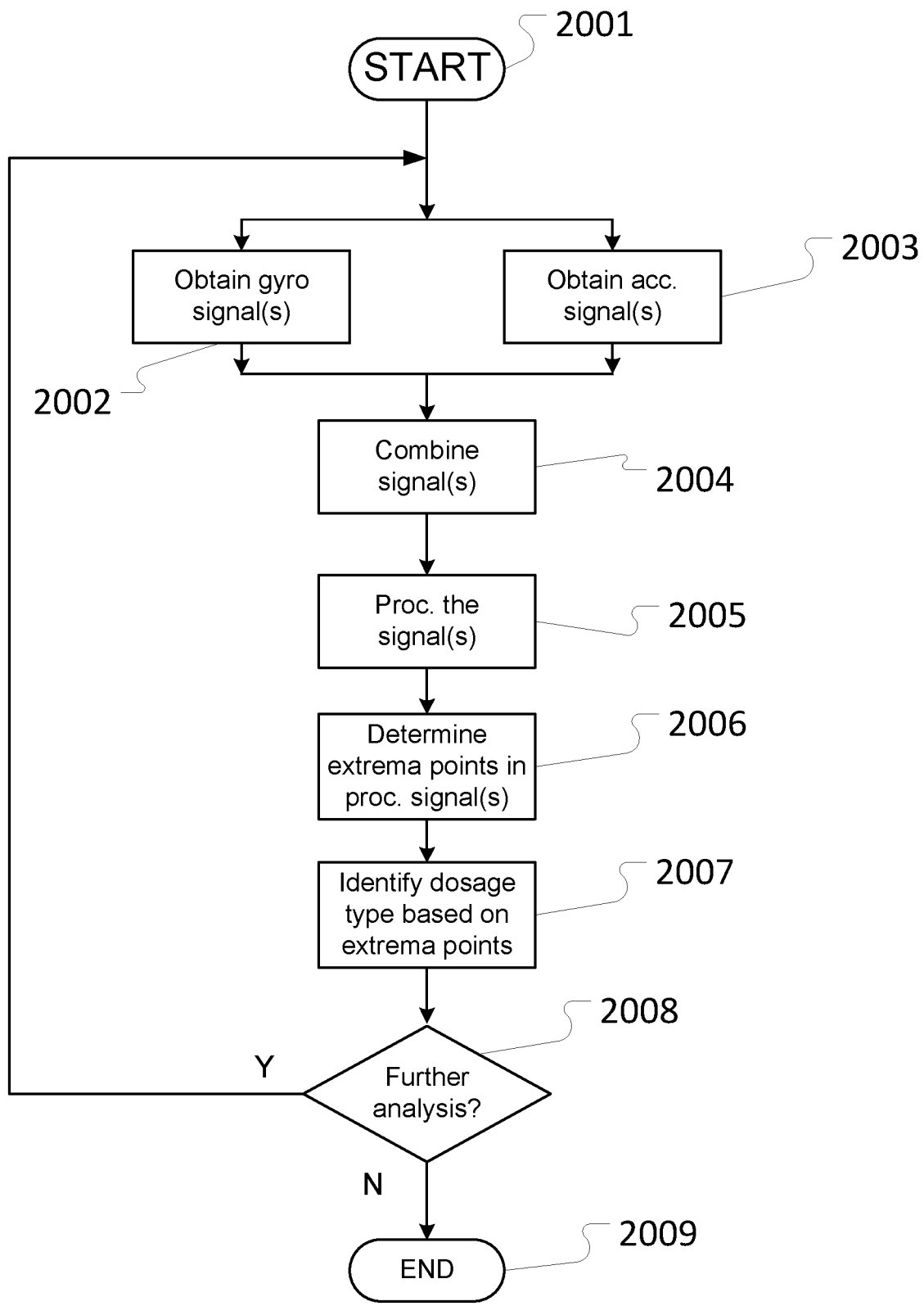
FIG. 20 schematically illustrates a flow chart of one embodiment of the dosage classification or determination of vibration signals aspect as disclosed herein.

FIG. 15b schematically illustrates an exemplary dosage classification signal obtained by processing at least some of the signals of FIG. 15a according to a dosage classification or identification aspect of the present invention as disclosed herein and with one embodiment thereof being illustrated in FIG. 20.

The result of FIG. 15b is obtained by processing the signals of FIG. 15a according to FIG. 20 or embodiments thereof and comprises identification of three distinct characteristic (local) extrema values-two (local) maximum and one (local) minimum value as indicated by the three circles. These extrema values may be used to determine as disclosed herein that a dosage increment of one unit was made using the liquid drug administration device by the user thereby enabling simple and reliable dosage classification or identification. For this and other identifications, additional criteria like the extrema being considered being above or within a given threshold or range (in value (y-axis in the Figure) and/or in time (x-axis in the Figure)), etc.

Figure 16A:
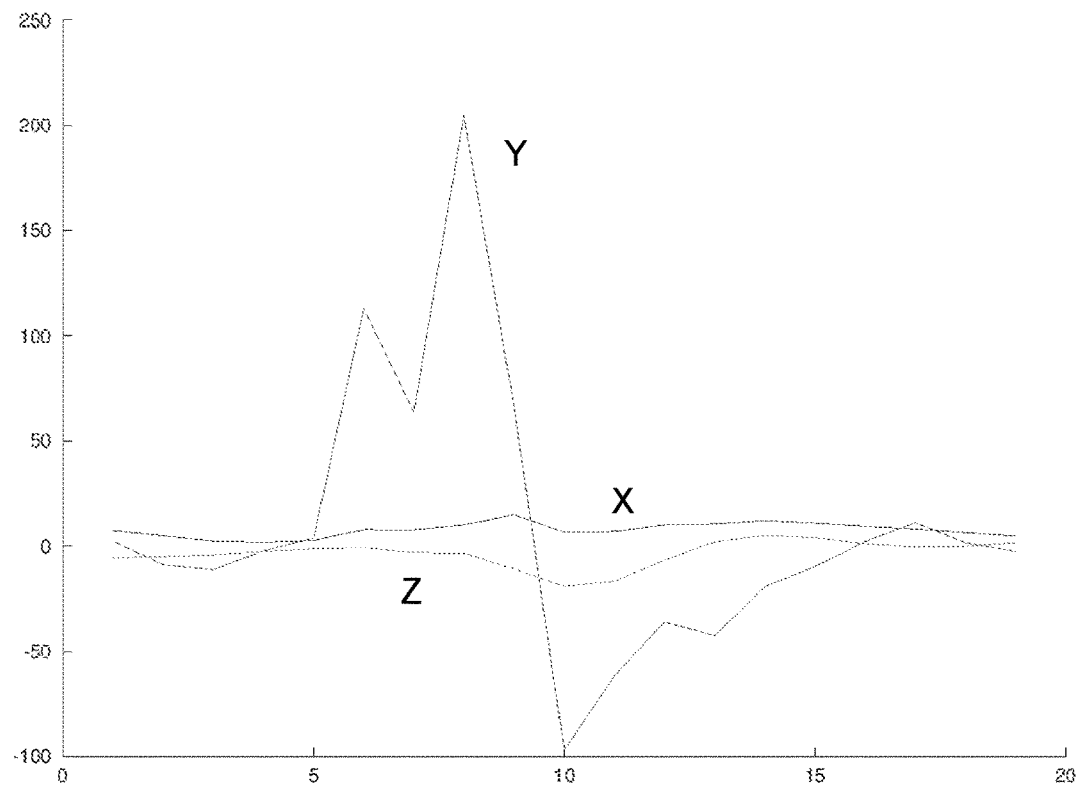
FIG. 16a schematically illustrates exemplary vibrations emitted by a liquid drug administration device, as measured by a gyrometer or similar, for a dosage increment of a second type.

FIG. 16a schematically illustrates exemplary vibrations emitted by a liquid drug administration device, as measured by a gyrometer or similar, for a dosage increment of a second type.

FIG. 16a illustrates three raw or unprocessed gyrometer signals as measured by a (three-axes) gyrometer or similar according to the exemplary reference coordinate system of FIG. 13 for a particular type of dosage determination device (and used vibration sensor) and particular type of liquid drug administration device.

One of the (second type) gyrometer signals (the signal obtained according to the y axis) is somewhat similar to the corresponding signal of the first type of FIG. 15a but has a slight decrease on its leading edge. Such differences between gyrometer signals of a first type and of a second type may e.g. be caused by a used sample rate when obtaining the gyrometer signals resulting in the first smaller peak (at value 6) to be skipped thereby producing a shape (due to the used sampling rate) of the first type instead of the second type. Reliable dosage determination or classification should be able to detect both types regardless of used sampling rate.

Figure 16B:
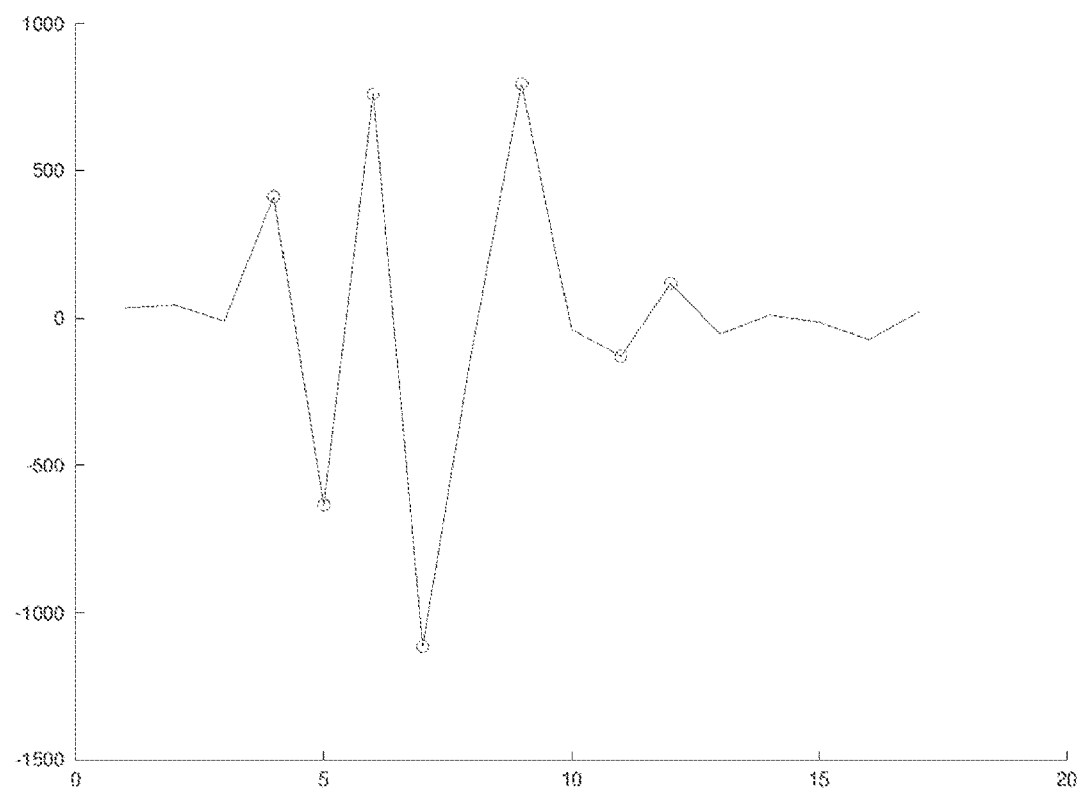
FIG. 16b schematically illustrates an exemplary dosage classification signal obtained by processing at least some of the signals of FIG. 16a according to the dosage classification or identification aspect as disclosed herein.

FIG. 16b schematically illustrates an exemplary dosage classification signal obtained by processing at least some of the signals of FIG. 16a according to the dosage classification or identification aspect as disclosed herein.

The result of FIG. 16b is obtained by processing the signals of FIG. 16a according to FIG. 20 or embodiments thereof and comprises identification of five distinct characteristic (local) extrema values-three (local) maximum and two (local) minimum values as indicated by the five leftmost (in the figure) circles in a somewhat 'w' shape. These extrema values may be used as disclosed to determine herein that a dosage increment of one unit (but for a vibration signal of a second type) was made using the liquid drug administration device by the user thereby enabling simple and reliable dosage classification or identification. In general, the extrema being considered are all above or within a given threshold or range (in value (y-axis in the Figure) and/or in time (x-axis in the Figure)). The two rightmost are disregarded as they do not match one or more sufficient criteria like pattern, threshold/ranges, etc.

Figure 17A:
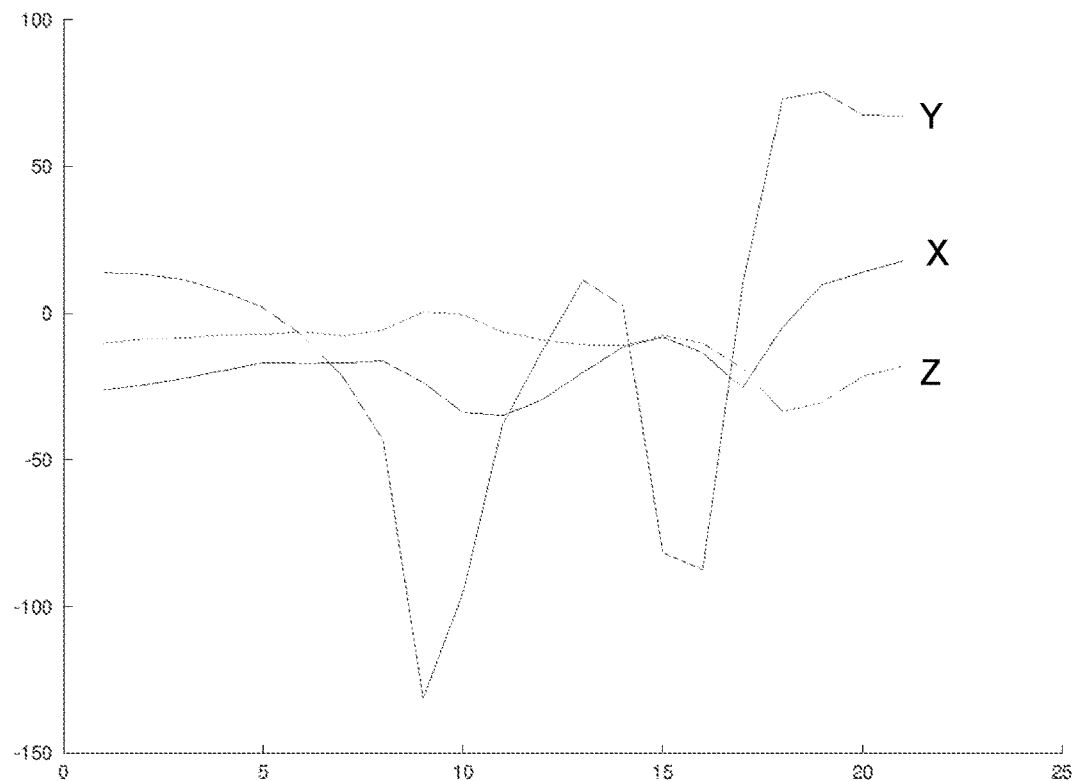
FIG. 17a schematically illustrates exemplary vibrations emitted by a liquid drug administration device, as measured by a gyrometer or similar, for two respective consecutive dosage decrements.

FIG. 17a schematically illustrates exemplary vibrations emitted by a liquid drug administration device, as measured by a gyrometer or similar, for two respective consecutive dosage decrements.

FIG. 17a illustrates three raw or unprocessed gyrometer signals as measured by a (three-axes) gyrometer or similar according to the exemplary reference coordinate system of FIG. 13 for a particular type of dosage determination device (and used vibration sensor) and particular type of liquid drug administration device.

Decrement vibrations signals are generally weaker in amplitude than increment vibration signals but are generally more consistent in shape.

Except for a dosage decrementation from 1 to 0 units, the decrement vibration signals all more or less have a same basic shape as seen in FIG. 17a (at least for the particular type of dosage determination device, used vibration sensor, and/or liquid drug administration device).

Figure 17B:
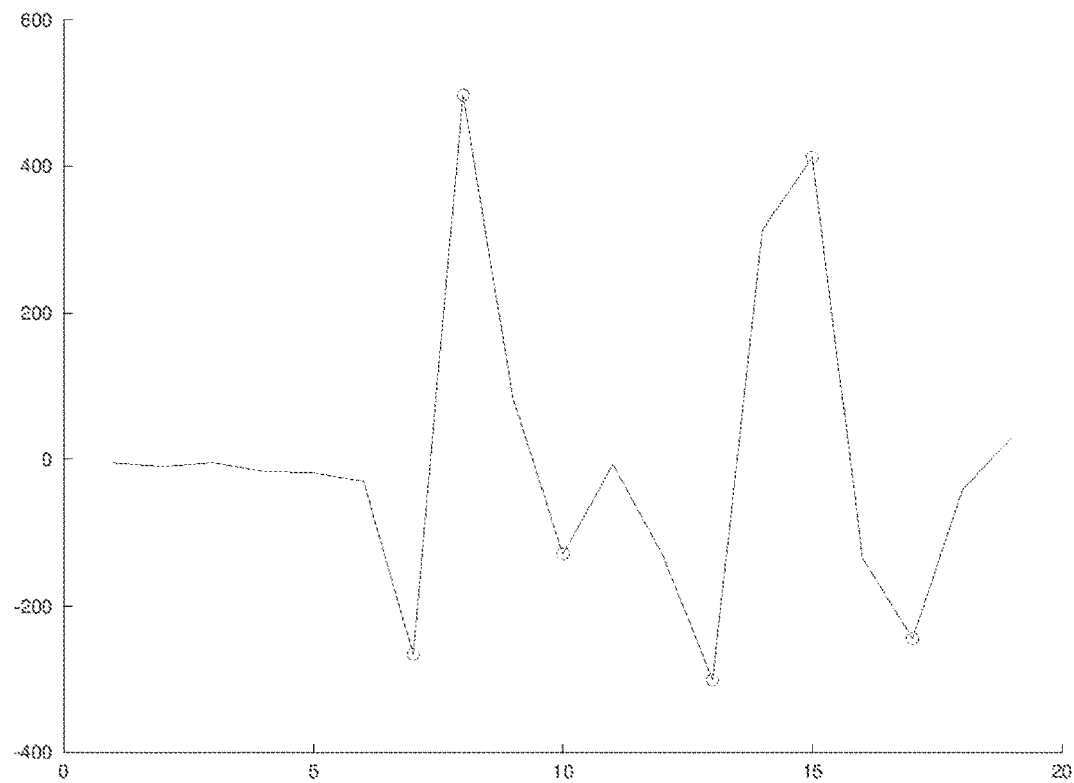
FIG. 17b schematically an exemplary dosage classification signal obtained by processing at least some of the signals of FIG. 17a according to the dosage classification or identification aspect as disclosed herein.

FIG. 17b schematically an exemplary dosage classification signal obtained by processing at least some of the signals of FIG. 17a according to the dosage classification or identification aspect as disclosed herein.

The result of FIG. 17b is obtained by processing the signals of FIG. 17a according to FIG. 20 or embodiments thereof and comprises identification of three distinct characteristic (local) extrema values for each dosage decrementation-one (local) maximum and two (local) minimum values-as indicated by the respective three circles. If the decrement adjustments are performed in very quick succession, one point (a minimum value) may be shared for two decrement vibration signals (e.g. as seen in FIG. 18b for dosage decrements from 5 units to 1 unit).

Figure 18A:
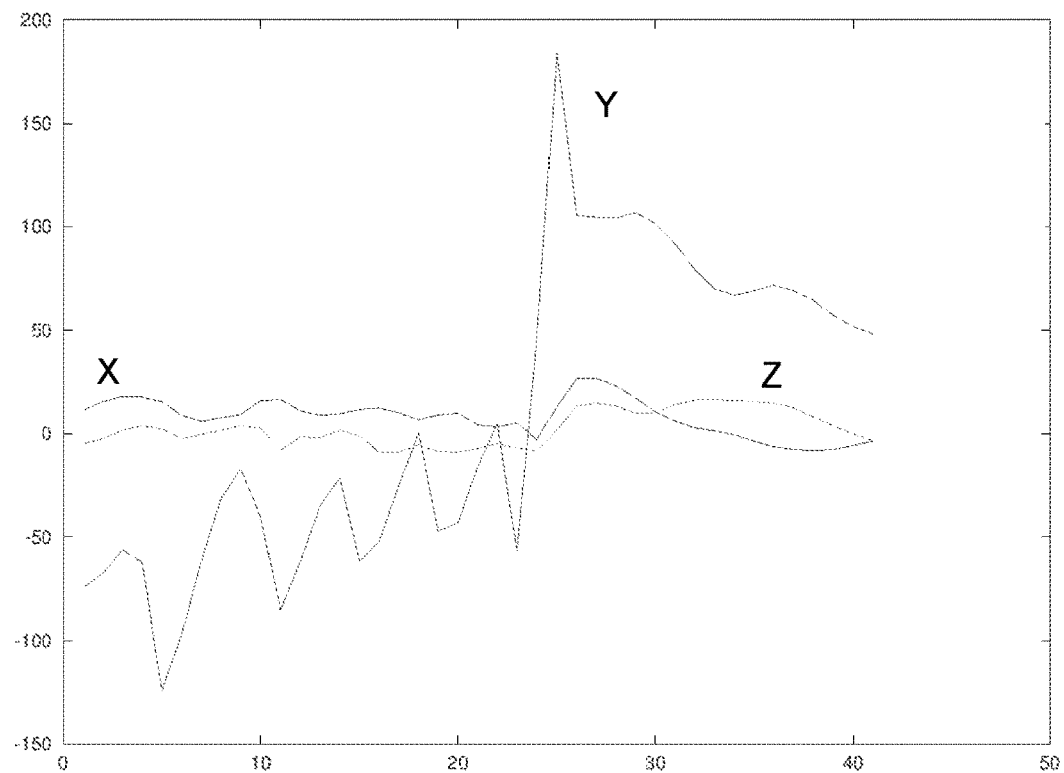
FIG. 18a schematically illustrates exemplary vibrations emitted by a liquid drug administration device, as measured by a gyrometer or similar, for five respective dosage decrements decrementing the set dose from 5 units to 0 units.

FIG. 18a schematically illustrates exemplary vibrations emitted by a liquid drug administration device, as measured by a gyrometer or similar, for five respective dosage decrements decrementing the set dose from 5 to 0 units.

As mentioned and as apparent from FIG. 18a, a dosage decrementation from 1 to 0 units will have a slightly different shape (at least for the particular type of dosage determination device, used vibration sensor, and/or liquid drug administration device).

Figure 18B:
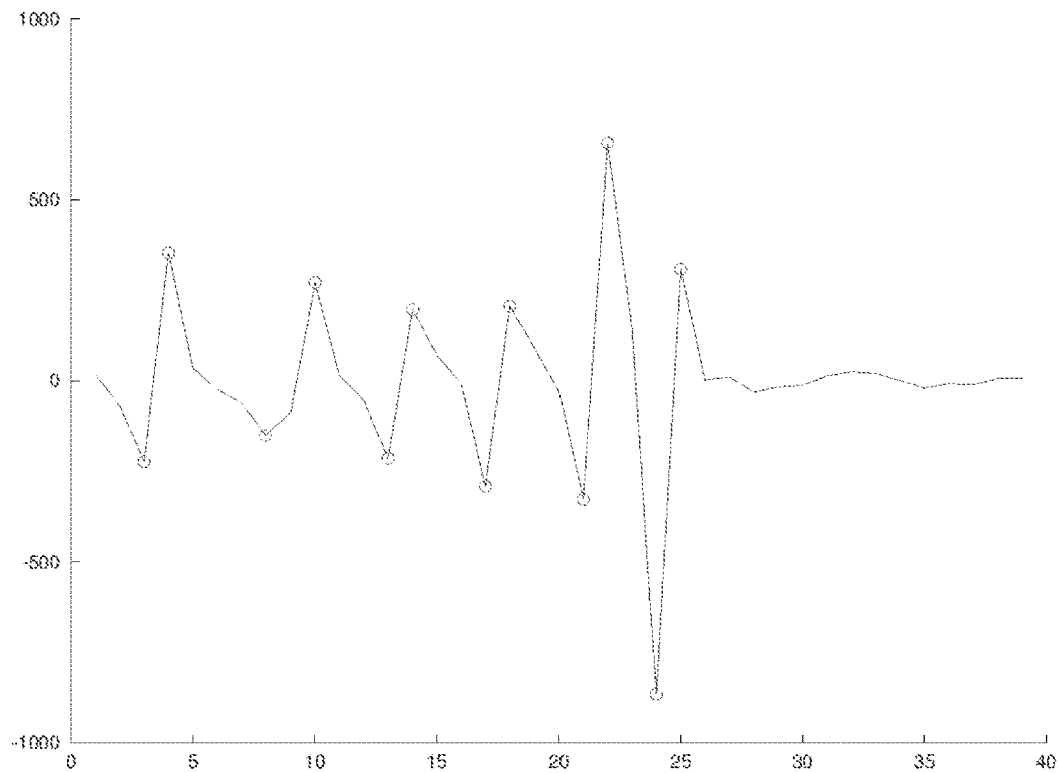
FIG. 18b schematically an exemplary dosage classification signal obtained by processing at least some of the signals of FIG. 18a according to the dosage classification or identification aspect as disclosed herein.

FIG. 18b schematically an exemplary dosage classification signal obtained by processing at least some of the signals of FIG. 18a according to the dosage classification or identification aspect as disclosed herein.

The result of FIG. 18b is obtained by processing the signals of FIG. 18a according to FIG. 20 or embodiments thereof and comprises identification of three distinct characteristic (local) extrema values (with overlap)-one (local) maximum and two (local) minimum values-for each dosage decrementation for the four dosage decrements from 5 units to 1 unit and identification of three distinct characteristic (local) extrema values-two (local) maximum and one (local) minimum value-for the dosage decrementation from 1 to 0 units.

Figure 19:
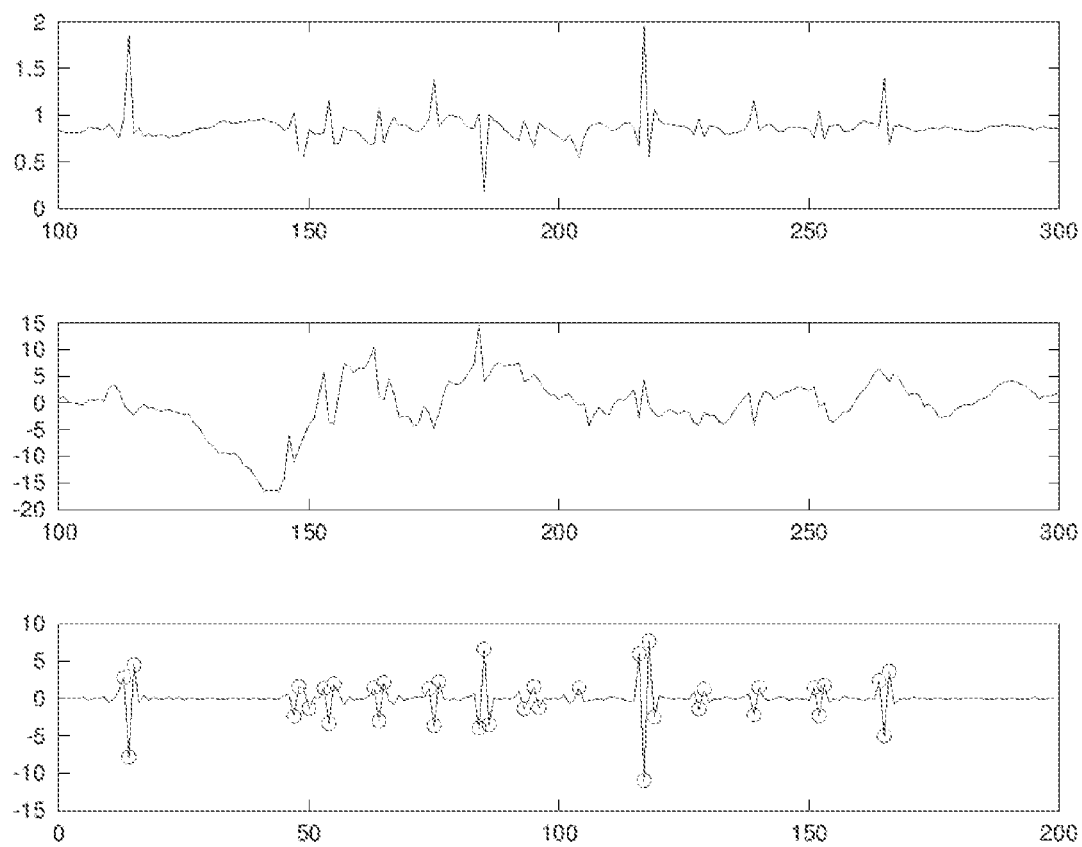
FIG. 19 schematically illustrates an exemplary accelerometer signal and an exemplary gyrometer signal obtained for injection of 12 doses of liquid drug injected by a liquid drug administration device as well as a resulting processed signal being processed as disclosed herein to enable dosage determination or classification of the signals.

FIG. 19 schematically illustrates an exemplary accelerometer signal and an exemplary gyrometer signal obtained for injection of 12 doses of liquid drug injected by a liquid drug administration device as well as a resulting processed signal being processed as disclosed herein to enable dosage determination or classification of the signals.

At least in some embodiments, identification or classification of dosage determination in relation to dosage injection is done using accelerometer signals obtained by a vibration determination element e.g. comprising a (three-axes) gyrometer or similar obtained according to the reference coordinate system of axes of FIG. 13 by rather than by using gyrometer signals. Alternatively, the identification or classification of dosage is done (alternatively or in addition) based on gyrometer signals. In some embodiments, only the accelerometer signal according to a single axis (i.e. the y axis or lengthwise axis) is used for the subsequent processing. Alternatively, a combined signal is used or a accelerometer signals according to several axes are used.

The result according to FIG. 19 (i.e. the bottom graph/signal) is obtained by processing the accelerometer signal (according to the y axis) of FIG. 19 (i.e. the upper graph/signal) according to FIG. 20 or embodiments thereof and comprises. In the processed resulting signal, each injection of one dose unit is identified or characterized by a number of distinct and separate characteristic (local) extrema values. These (local) extrema values indicating injection of one dose are either two (local) extrema values being a minimum followed by a maximum (within a certain time window, within a certain threshold or range of values, etc.) or three (local) extrema values being a maximum, followed by a minimum, and followed by a maximum (within a certain time window, within a certain threshold or range of values, etc.).

During an injection process (at least for most current practical implementations), a dosage dialer or similar will typically step back through the dosage indications to zero. The injection of each individual drug units will thus typically be spaced apart in time depending on a resistance of the material being injected into, e.g. between about 30 to about 60 milliseconds. This knowledge allows false positives, such as the first group of the three leftmost local extrema in FIG. 19, to actively be disregarded.

FIG. 20 schematically illustrates a flow chart of one embodiment of the dosage classification or determination of vibration signals aspect as disclosed herein.

The method starts or initiates at step 2001 and at steps 2002 and 2003 one or more gyrometer signals and one or more accelerometer signals are respectively obtained. Steps 2002 and 2003 may be done at the same time (and e.g. by the same vibration sensor). The vibration sensor may e.g. be a six degree of freedom (DoF) inertial measurement unit (IMU) providing signals indicative of translational movement according to three perpendicular axes and rotational movement about the same three perpendicular axes (denoted x, y, and z) according to a reference coordinate system of axes e.g. as illustrated in FIG. 13. The respective signals may be obtained as continuous signals or obtained as (or converted to) discrete signals sampled at an appropriate sample rate. Preferably, the relevant signals are provided as discrete signals.

In some embodiments, only gyrometer signal(s) is/are used and in other alternative embodiments only accelerometer signal(s) is/are used.

In some other embodiments both gyrometer signal(s) and accelerometer signal(s) is/are used e.g. for different purposes as explained in the following.

In at least some embodiments, an optional step 2004 is carried out that combines the obtained signals in an expedient way to reduce noise, suppress irrelevant features, and/or to enhance or amplify relevant features of the respective signals.

According to some embodiments (with three obtained vibration signals), a combined signal is produced by taking the amplitude of a signal according to one (primary or most significant) axis (preferably according to the y or lengthwise axis of the liquid drug administration device) and dampening or reducing it by the sum of the amplitudes of the other (non-primary) axes (preferably the x and z axes). This makes the resulting signal more robust in relation to noise as vibrations from other sources such as by placing the device on a table, tapping the device, dropping it, etc. are unlikely to affect only one axes on the gyroscope. The signal in such embodiments is thus showing only vibrations affecting the primary axis exclusively which are more likely to be produced from within the drug injection device than from the outside.

This can be done both for the gyrometer signals and the accelerometer signals (then with six obtained vibration signals), i.e. resulting in a combined gyrometer signal and a combined accelerator signal.

In alternative or further embodiments, one single combined gyrometer signal and one single combined accelerometer signal is obtained as explained just above (requiring in three gyrometer signals according to three axes and three accelerometer signals according to three axes) where a further combined signal is generated based on the combined gyrometer signal and the combined accelerometer signal. In some embodiments, the further combined signal is generated e.g. by subtracting the combined accelerometer signal from the combined gyrometer signal. This e.g. ensures that the signals were not produced e.g. by sudden movement of the device(s), but much more likely by vibrations from activities (increment, decrement, and/or injection).

Alternatively, other ways of combining the signals in expedient ways could be used.

Separate determination may e.g. be done for a number of signals (e.g. a number of combined signals) and determine for each whether a dosage activity is identified and deciding that the dosage activity is determined to be present only if a majority or all of the separate determinations indicates the presence of the dosage activity in question.

One determination may e.g. be done for one or more accelerometer signals (e.g. a combined signal) and another separate determination may e.g. be done for one or more gyrometer signals (e.g. a combined signal) and only if both agree that a same dosage activity is identified, the overall result will be that. This increases the robustness of determination and/or reduces the likelihood e.g. of false positives.

Any one of these combinations reduces computational complexity (and thereby computation effort and power consumption), reduces noise in the signals, and/or increases the quality of the signals for the purposes of dosage classification or determination based on vibration signals.

At step 2005, the signals (depending on specific embodiment-the obtained gyrometer and/or obtained accelerometer signal(s) or one or more combined signals thereof) are processed as disclosed herein.

More specifically, the relevant signal(s) are processed by taking the derivative thereof. In this way, a signal is produced that amplifies relevant features and suppresses irrelevant features. In preferred embodiments, the derivative is applied twice (i.e. the second derivate is applied to the result of taking the first derivative or a second order derivative is taken of the relevant signal(s)). This sort of provides a measure of "acceleration" of change of the respective signal(s) and further increases relevant and reduces irrelevant characteristics for determination of dosage activity. Higher order (than two) derivatives (than two) may also be used.

Accordingly, the processing reliably and robustly amplifies the vibration signals even in the presence of other movements and rotations.

The respective signals of FIGS. 15b, 16b, 17b, 18b, and lower signal/graph of FIG. 19 shows the result of this processing (derivative taken twice) of exemplary vibration signals as explained previously.

At step 2006, the resulting processed signal(s) (from step 2005) is/are processed further or analyzed in order to determine (local) extrema values of the signal(s). Any suitable way of determining (local) extrema may be used. According to some embodiments, (local) extrema values are determined by subtracting the previous value of the signal and determining where the difference changes sign (i.e. goes from a positive value to a negative value or vice versa). To limit the extrema values to be considered a suitable threshold for the absolute value of the extrema can be applied. As an example, in FIG. 17b, the points in the interval [5;10] have the approximate values (−10, −20, −250, 500, 100, −100, 0). The difference between the points are therefore (_, −10, −230, 750, −400, —200, 100). The change in sign in the difference occurs at point 7, 8 and 10, which are marked in FIG. 17b with circles.

When the (local) extrema has been identified these are used as input at step 2007 where they are used to identify patterns within the processed signals corresponding or correlating with predetermined patterns respectively being associated with dosage increments, dosage decrements, and injection of a unit of a liquid drug as disclosed herein.

As mentioned at least according to some embodiments,
a pattern of three (local) extrema of a gyrometer vibration signal having (local) maximum, followed by (local) minimum, and followed by (local) maximum identify a signal in question to have dosage increment (of a first type);
a pattern of five (local) extrema of a gyrometer vibration signal being in a 'w' shape identify a signal with a dosage increment (of a second type);
a pattern of three (local) extrema of a gyrometer vibration signal being (local) minimum, followed by (local) maximum, and followed by (local) minimum identify a signal with a dosage decrement (not decrementing from 1 to 0 units);
a pattern of four (local) extrema of a gyrometer vibration signal having (local) minimum, followed by (local) maximum, followed by (local) minimum, and followed by (local) maximum identify a signal with a dosage decrement decrementing from 1 to 0 units; and
a pattern of three (local) extrema of an accelerometer vibration signal having a local maxima, followed by a local minima, followed by a local maxima, where the local maxima are in the same order of magnitude identify a signal with dosage injection of one unit.

For each of these classifications, the distance (in samples/time) between the local extrema is checked to fall within predefined ranges to provide an actual identification.

As mentioned, the predetermined patterns being used may be dependent at least to an extent by a specific type of a dosage determination device implementing this method, a specific make of the used vibration sensor(s), and a specific type liquid drug administration device that the method is used for.

At step 2008 it is determined whether the dosage classification or determination of vibration signals should be continued or not. If yes, the method loops back to before step 2002 and 2003 and if no the method ends at step 2009.

The method according to FIG. 20 provides reliable dosage classification or determination of vibration signals that furthermore allows the needed processing to be performed on relatively resource constrained embedded devices (in terms of power, memory, and/or processing capabilities) in particular if discrete signals are used.

It is noted that step 2004 could e.g. be carried out after step 2005, whereby processed signals (derivative signals) are combined as disclosed herein rather than combining before processing as disclosed herein.

The method may also readily be used for dosage classification or determination of sound signals instead of vibration signals (then having a step of obtaining at least one sound signal (several can be provided from several sound sources) instead of step 2002 and step 2003. If only a single sound signal is used, the combination step 2004 is not needed or used.

In some further embodiments, the method may combine a step of obtaining at least one sound signal in addition to step 2002 and/or step 2003 where dosage classification or determination may be done separately as disclosed herein for the sound signal(s) and the vibration signal(s) and then determine or classify a particular dosage adjustment (increment, decrement, or injection) only if both indicate the presence of a particular dosage adjustment. This is advantageous, since each separate way (sound and vibration) may have different inherent tradeoff between recall and precision where increasing recall will decrease precision and vice versa. Using both ways (being uncorrelated sources) can increase recall for both ways while retaining precision by requiring that both ways need to agree on a dosage determination or classification.

In some embodiments, only an accelerometer signal according to a single axis (the y or lengthwise axis) is used for determining dosage injection simplifying subsequent processing.

In some specific embodiments, three orthogonal gyrometer signals (e.g. combined as explained), three orthogonal accelerometer signals (e.g. combined as explained) or one primary accelerometer signal (y or lengthwise axis), all e.g. provided by a single six degree of freedom IMU, is used where the (e.g. combined) gyrometer signals is used for determining dosage increments and decrements and where the accelerometer signal(s) (e.g. combined) is used for determining dosage injection.

In some embodiments as disclosed herein, the position determination device and/or the dosage determination device further comprises a temperature sensor configured to continuously monitor whether the liquid drug is kept at safe temperature. A warning may be given before the temperature reaches levels that will make the liquid drug unfit for use. This warning may be given using audiovisual cues and/or by the separate electric device.

According to an alternate aspect of the invention, image recognition may be used as a method of locating injection sites. In some embodiments this may be achieved by using an image sensor that is e.g. hand held by the user or mounted on e.g. a pair of glasses or elsewhere on the user. The image produced by the image sensor would then e.g. be digitally processed to identify the liquid drug administration device 200, an injection region or location, and a location of the liquid drug administration device in relation to the injection region or location. This may be achieved by using any suitable image processing techniques such as but not limited to e.g. edge detection, ANN (artificial neural networks), DNN (deep neural networks), or some combination or derivation hereof.

In some embodiments image recognition may be used to augment or supplement the position determination techniques described herein. For example, the image recognition could add a second source of data to the movement or other based technique(s) as disclosed herein thus improving precision and/or reliability further. In other embodiments, image recognition could be used to determine actual starting points of the movement of hand and drug administration device thus reducing the need for fixed calibration.

Even though, the description mainly mentions user-administrated injection where a person to receive the liquid drug is also the user to administer the drug it is to be understood that at least for certain aspects, the user may e.g. be a medical professional or the like administering the liquid drug to another person.

Some of the different components are only disclosed in relation to a single embodiment of the invention, but is meant to be included in the other embodiments without further explanation.

Some preferred embodiments have been shown in the foregoing, but it should be stressed that the invention is not limited to these, but may be embodied in other ways within the subject matter as defined in the following claims.

In the claims enumerating several features, some or all of these features may be embodied by one and the same element, component or item. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, elements, steps or components but does not preclude the presence or addition of one or more other features, elements, steps, components or groups thereof.

The invention claimed is:

1. A dosage determination device for determining a dosage activity performed by a liquid drug administration device, the dosage determination device being configured to
    obtain at least one vibration signal from a vibration determination element, the vibration determination element being configured to obtain the at least one vibration signal in response to registering vibration of the liquid drug administration device,
    wherein the dosage determination device further comprises one or more processing units configured to
    provide a first processed signal by deriving a derivative or a second order derivative on the basis of at least a part of the at least one vibration signal,
    determine a number of local extrema in the first processed signal resulting in a number of determined local extrema, and
    processing the number of determined local extrema by matching against predetermined patterns of groups of local extrema, each group of predetermined local extrema representing a particular associated dosage activity, thereby determining whether at least one dosage activity is indicated to be present in the at least one vibration signal, and
    wherein the at least one vibration signal comprises a plurality of gyrometer vibration signals and a plurality of accelerometer vibration signals and wherein the one or more processing units are configured to
    derive a first combined signal on the basis of the plurality of gyrometer vibration signals, and
    derive a second combined signal on the basis of the plurality of accelerometer vibration signals.

2. The dosage determination device according to claim 1, wherein the vibration determination element comprises at least one gyrometer and/or at least one accelerometer and wherein the at least one vibration signal obtained by the dosage determination device comprises at least one gyrometer vibration signal or at least one accelerometer vibration signal.

3. The dosage determination device according to claim 2, wherein the vibration determination element is a six degree of freedom inertial measurement unit providing six signals respectively indicative of translational movement along three predetermined perpendicular axes and of rotational movement about the three predetermined perpendicular axes, whereby the least one vibration signal comprises three orthogonal gyrometer vibration signals and three orthogonal accelerometer vibration signals.

4. The dosage determination device according to claim 1 wherein the at least one vibration signal comprises a plurality of vibration signals and wherein the one or more processing units are further configured to
    derive a combined signal on the basis of at least some, e.g. all, of the plurality of vibration signals, and
    provide the first processed signal by deriving a derivative or a second order derivative of the combined signal instead of on the basis of at least a part of the at least one vibration signal.

5. The dosage determination device according to claim 4, wherein the one or more processing units are configured to derive the combined signal by subtracting an amplitude of one of the plurality of vibration signals by an amplitude of at least one other of the plurality of vibration signals.

6. The dosage determination device according to claim 1, wherein the one or more processing units are configured to derive a third combined signal on the basis of the first combined signal and the second combined signal.

7. The dosage determination device according to claim 6, wherein the one or more processing units are configured to derive the third combined signal by subtracting the second combined signal from the first combined signal.

8. The dosage determination device according to claim 1, wherein the dosage determination device is configured to
    obtain at least one sound signal from at least one sound sensor configured to register one or more distinct sounds caused by the drug administration device when operated by a user to perform the dosage activity, and
    provide the first processed signal on the basis of at least a part of the at least one sound signal instead or in addition to at least a part of the at least one vibration signal.

9. The dosage determination device according to claim 8, wherein the dosage determination device is configured to
    determine whether at least one dosage activity is indicated to be present in the at least one vibration signal,
    determine whether at least one dosage activity is indicated to be present in the least one sound signal, and
    deciding that at least one dosage activity is determined only if the at least one dosage activity is determined to be present in both the at least one vibration signal and the least one sound signal.

* * * * *